US007951920B2

(12) United States Patent
Brandt et al.

(10) Patent No.: US 7,951,920 B2
(45) Date of Patent: May 31, 2011

(54) CONJUGATE OF AN ANTIBODY AGAINST CCR5 AND AN ANTIFUSOGENIC PEPTIDE

(75) Inventors: Michael Brandt, Iffeldorf (DE); Stephan Fischer, Polling (DE); Erhard Kopetzki, Penzberg (DE); Suryanarayana Sankuratri, San Jose, CA (US); Ralf Schumacher, Penzberg (DE)

(73) Assignee: Roche Palo Alto LLC, Palo Alto, CA (US)

( * ) Notice: Subject to any disclaimer, the term of this patent is extended or adjusted under 35 U.S.C. 154(b) by 272 days.

(21) Appl. No.: 11/893,899

(22) Filed: Aug. 17, 2007

(65) Prior Publication Data

US 2009/0028881 A1    Jan. 29, 2009

(30) Foreign Application Priority Data

Aug. 17, 2006 (EP) .................................. 06017156
Sep. 29, 2006 (EP) .................................. 06020647

(51) Int. Cl.
*C07K 17/00*     (2006.01)
*C07K 17/14*     (2006.01)
*C12P 21/08*     (2006.01)
*A61K 39/00*     (2006.01)

(52) U.S. Cl. ............... 530/391.1; 424/178.1; 530/391.7

(58) Field of Classification Search .................. None
See application file for complete search history.

(56) References Cited

U.S. PATENT DOCUMENTS

| 5,202,238 | A | 4/1993 | Fell et al. |
| 5,204,244 | A | 4/1993 | Fell et al. |
| 5,464,933 | A | 11/1995 | Bolognesi et al. |
| 5,656,480 | A | 8/1997 | Wild et al. |
| 5,871,732 | A | 2/1999 | Burkly et al. |
| 5,876,969 | A | 3/1999 | Fleer et al. |
| 6,013,263 | A | 1/2000 | Barney et al. |
| 6,017,536 | A | 1/2000 | Barney et al. |
| 6,060,065 | A | 5/2000 | Barney et al. |
| 6,093,794 | A | 7/2000 | Barney et al. |
| 6,136,310 | A | 10/2000 | Hanna et al. |
| 6,258,782 | B1 | 7/2001 | Barney et al. |
| 6,348,568 | B1 | 2/2002 | Barney et al. |
| 6,479,055 | B1 | 11/2002 | Bolognesi et al. |
| 6,528,625 | B1 | 3/2003 | Wu et al. |
| 6,610,834 | B1 | 8/2003 | Lobo |
| 6,656,906 | B1 | 12/2003 | Barney et al. |
| 7,138,496 | B2 | 11/2006 | Hua et al. |
| 2001/0000241 | A1 | 4/2001 | Li et al. |
| 2002/0048786 | A1 | 4/2002 | Rosen et al. |
| 2002/0061834 | A1 | 5/2002 | Rosen et al. |
| 2002/0106374 | A1 | 8/2002 | Olson et al. |
| 2002/0146415 | A1 | 10/2002 | Olson et al. |
| 2002/0147147 | A1 | 10/2002 | Molling et al. |
| 2002/0147311 | A1 | 10/2002 | Gillies et al. |
| 2003/0003440 | A1 | 1/2003 | Lopalco |
| 2003/0044411 | A1 | 3/2003 | Olson et al. |
| 2003/0049227 | A1 | 3/2003 | Gillies et al. |
| 2003/0049251 | A1 | 3/2003 | Barbas et al. |
| 2003/0099645 | A1 | 5/2003 | Lobo |
| 2003/0100058 | A1 | 5/2003 | Roschke et al. |
| 2003/0103984 | A1 | 6/2003 | Kohler |
| 2003/0104581 | A1* | 6/2003 | Hoess et al. ................. 435/69.7 |
| 2003/0152913 | A1 | 8/2003 | Hua et al. |
| 2003/0165988 | A1 | 9/2003 | Hua et al. |
| 2003/0166024 | A1 | 9/2003 | Rosen et al. |
| 2003/0166870 | A1 | 9/2003 | Wu et al. |
| 2003/0195348 | A1 | 10/2003 | Combadiere et al. |
| 2003/0215421 | A1 | 11/2003 | McDonald et al. |
| 2003/0226155 | A1 | 12/2003 | Sadeghi et al. |
| 2003/0228306 | A1 | 12/2003 | Olson et al. |
| 2004/0043033 | A1 | 3/2004 | Green |
| 2005/0008649 | A1 | 1/2005 | Shin et al. |
| 2005/0100991 | A1 | 5/2005 | Rosen et al. |
| 2005/0114037 | A1 | 5/2005 | Desjarlais et al. |
| 2006/0051346 | A1 | 3/2006 | Wijdenes |
| 2006/0121480 | A1 | 6/2006 | Fung |
| 2007/0036796 | A1* | 2/2007 | Brandt et al. ............... 424/155.1 |

FOREIGN PATENT DOCUMENTS

| EP | 0 512 112 B1 | 11/1991 |
| EP | 0 307 434 B1 | 9/1993 |
| EP | 0 512 112 B1 | 5/1997 |
| EP | 0 442 724 B1 | 10/1999 |
| EP | 1 207 202 A1 | 5/2002 |
| EP | 0 840 618 B1 | 4/2003 |
| EP | 1 161 456 B1 | 12/2004 |
| EP | 1 266 965 B1 | 5/2006 |
| EP | 0 854 885 B1 | 12/2006 |
| EP | 1 346 731 B1 | 12/2006 |
| EP | 1 144 006 B1 | 10/2007 |
| WO | WO 91/09966 A1 | 7/1991 |
| WO | WO 92/09305 A1 | 6/1992 |
| WO | WO 94/26910 A1 | 11/1994 |

(Continued)

OTHER PUBLICATIONS

Rudikoff, Giusti, Cook, and Scharff. Single amino acid substitution altering antigen binding specificity. Proceedings of the National Academy of Sciences, 1982. vol. 79, pp. 1979-1893.* Mac Callum, Martin, and Thronton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemcial and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*

(Continued)

*Primary Examiner* — Anne M. Gussow
(74) *Attorney, Agent, or Firm* — Robert C. Hall

(57) ABSTRACT

The current invention is related to a conjugate comprising one or more antifusogenic peptides and an anti-CCR5 antibody (mAb CCR5) characterized in that one to eight antifusogenic peptides are each conjugated to one terminus of the heavy and/or light chains of the anti-CCR5 antibody and to the pharmaceutical use of the conjugate.

5 Claims, 3 Drawing Sheets

FOREIGN PATENT DOCUMENTS

| | | |
|---|---|---|
| WO | WO 96/40191 A1 | 12/1996 |
| WO | WO 97/46697 A2 | 12/1997 |
| WO | WO 98/33523 A1 | 8/1998 |
| WO | WO 98/52976 A1 | 11/1998 |
| WO | WO 99/59615 A1 | 11/1999 |
| WO | WO 00/34317 A2 | 6/2000 |
| WO | WO 00/69902 | 11/2000 |
| WO | WO 01/42308 A2 | 6/2001 |
| WO | WO 01/43779 A2 | 6/2001 |
| WO | WO 01/58915 A2 | 8/2001 |
| WO | WO 01/58916 A2 | 8/2001 |
| WO | WO 02/22077 A2 | 3/2002 |
| WO | WO 02/083172 A1 | 10/2002 |
| WO | WO 03/033666 A2 | 4/2003 |
| WO | WO 03/066830 A2 | 8/2003 |
| WO | WO 03/072766 A1 | 9/2003 |
| WO | WO 2004/029074 A2 | 4/2004 |
| WO | WO 2004/085505 A2 | 10/2004 |
| WO | WO 2004/101739 A2 | 11/2004 |
| WO | WO 2004/103312 A2 | 12/2004 |
| WO | WO 2004/108885 A2 | 12/2004 |
| WO | WO 2005/067960 A1 | 7/2005 |
| WO | WO 2006/103100 A2 | 10/2006 |
| WO | WO 2007/045463 A1 | 4/2007 |
| WO | WO 2007/045465 A1 | 4/2007 |

OTHER PUBLICATIONS

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, McKay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Wang, L.X. et. al., "Carbohydrate-Centered Maleimide Cluster as a New Type of Templates for Multivalent Peptide Assembling: Synthesis of Multivalent HIV-1 gp41 Peptides," Bioorganic & Medicinal Chem. (2003) vol. 11, Issue 1, pp. 159-166.

Wild, C. et al., "Propensity for a Leucine Zipper-like Domain of Human Immunodeficiency Virus Type 1 gp41 to Form Oligomers Correlates with a Role in Virus-induced fusion rather than assembly of the Glycoprotein Complex," Proc. Natl. Acad. Sci. (1994) vol. 91, pp. 12676-12680.

Bar, S. et. al. "Role of the Ectodomain of the gp41 Transmembrane Envelope Protein of Human Immunodeficiency Virus type 1 in late Steps of the Membrane Fusion Process," J. Virology, 2004, vol. 78 (2), pp. 811-820.

Brady, et. al. "The Structure of CD4," Curr. Topic Microbiol. Immunol. 1996, vol. 205, pp. 1-17.

Brenneman, et. al. "Acquired Immune Deficiency Syndrome and the Developing Nervous System," International Rev. Neurobiology, 1990, vol. 32, pp. 305-353.

Brunhouse, R., et al.,"Isotypes of IgG: Comparison of the Primary Stuctures of Three Pairs of Isotypes which Differ in their Ability to Activate complement," Molecular Immunology. 16 (1979) 907-917.

Burnette, "Western Blotting: Electrophoretic Transfer of Proteins from Sodium Dodecyl Sulfate-Polyacrylamide Gels to Unmodified Nitrocellulose and Radiographic Detection with Antibody and Radioiodinated Protein A," Analytical Biochem. 1981, vol. 112, pp. 195-203.

Burton, D.R. et. al., "The C1q Receptor Site on Immunoglobulin G," Nature (1980) vol. 288, pp. 338-344.

Cohen, J. "Likely HIV Cofactor Found," Science 1996, vol. 272, pp. 809-810.

Cocchi, F. et. al., "Identification of RANTES, MIP-1α, and MIP-1β as the Major HIV-Suppressive Factors Produced by CD8+ T Cells," Science (1995) vol. 270 pp. 1811-1815.

Dean, M., et al., "Genetic Restriction of HIV-1 Infection and Progression to AIDS by a Deletion Allele of the CKR5 Structural Gene," Science 273 (1996) 1856-1862.

Edelman, G.M., et al., "The Covalent Structure of an Entire_G Immunoglobin Molecule," Natl. Acad. Sci. USA 63 (1969) 78-85.

Hawlisch, et. al. "Site-Directed C3a Receptor Antibodies from Phage Display Libraries," American Assoc. Immunol., 1998 vol. 160, pp. 2947-2958.

Herareh, M., et al., "Effector Function Activities of a Panel of Mutants of a Broadly Neutralizing Antibody against Human Immunodeficiency Virus Type 1," J of Virology 75 (2001) 12161-12168.

Huston, J.S. et. al., "Protein Engineering of Single-Chain Fv Analogs and Fusion Proteins," Methods in Enzymology (1991) vol. 203, pp. 46-88.

Idusogie E.E., et al., "Mapping of the C1q Binding Site on Rituxan, a Chimeric Antibody with a Human IgG1 Fc," J. Immunology 164 (2000) 4178-4184.

Johnson, G., et al., "Kabat Database and its applications: 30 years after the first variability plot," Nucleic Acids Research 28 (2000) 214-218.

Kazmierski, W.M., et. al., "CCR5 Cemokine Receptors: Gatekeepers of HIV-1 Infection," Current Drug Targets Infect. Disord. (2002) vol. 2, pp. 265-278.

Koyanagi, et. al. "Dual Infection of the Central Nervous System by AIDS Virus with Distinct Cellular Tropisms," Science, 1987, vol. 236, pp. 819-822.

Kreitman, et. al. "Mik-β1(Fv)-PE40, A Recombinant Immunotoxin Cytotoxic toward Cells Bearing the β-Chain of the IL-2 receptor," J. Immunol. 1992, vol. 149 (8), pp. 2810-2815.

Lee, et. al. "Epitope Mapping of CCR5 Reveals Multiple Conformational States and Distinct but Overlapping Structures Involved in Chemokine and Coreceptor Function," J. Biol. Chem. 1999, vol. 274 (14), pp. 9617-9626.

Lehner, T. et. al., "The Role of CCR5 Chemokine Ligands and Antibodies to CCR5 Coreceptors in Preventing HIV Infection," Trends Immunol. (2002) vol. 23, pp. 347-351.

Lonberg, "Human Antibodies from Transgenic Animals," Nature Biotechnol., 2005, vol. 23 (9), p. 1117-1125.

Lukas, T.J., et al., "Inhibition of C1-Mediated Immune Hemolysis by Monomeric and Dimeric Peptides from the Second Constant Domain of Human Immunoglobulin $G^1$," Journal of Immunology 127 (1981) 2555-2560.

Lund, J., et al., "Oligosaccharide-protein Interations in IgG can Modulate Recognition by Fcγ Receptors," FASEB 9 (1995) 115-119.

Meissner, P. et. al. "Transcient Gene Expression: Recombinent Protein Production with Suspension-Adapted HEK293-EBNA Cells," Biotechnology and Bioeng. 2001, vol. 75 (2), pp. 197-203.

Morgan, A., et al., "The N-terminal end of the $C_H2$ Domain of Chimeric Human IgG1 Anti-HLA-DR is necessary for C1q, FcγRI and FcγRIII Binding," Immunology 86 (1996) 319-324.

Morrison, S.L., et al., "Chimeric Human Antibody Molecules: Mouse Antigen-binding Domains with Human Constant Region Domains," Proc. Natational. Acad. Science USA 81 (1984) 6851-6855.

Mueller, A. et. al. "Molecules in Focus the Chemokine Receptor, CCR5," Int. J. Biochem., 2004, vol. 36, pp. 35-38.

Neuberger, M.S. et al., "A Hapten-specific Chimaeric IgE Antibody with Human Physiological Effector Function," Nature 314 (1985) 268-270.

Neuberger, M.S. et al. "Expression and regulation of Immunoglobulin Heavy Chain Gene Transfected into Lymphoid Cells," The EMBO Journal, 1983, vol. 2 (8), pp. 1373-1378.

Olson, W.C., et al., "Differential Inhibition of Human Immunodeficiency Virus Type 1 Fusion, gp120 Binding, and CC-Chemoking Activity by Monoclonal Antibodies to CCR5," Journal of Virology 73 (1999) 4145-4155.

Otaka, A. et. al., "Remodeling of gp41-C34 peptide leads to Highly Effective Inhibitors of the Fusion of HIV-1 with Target Cells," Angew. Chem. Int. Ed. 2002, vol. 41 (16), pp. 2937-2940.

Queen, C., et al., "A Humanized Antibody that binds to the Interleukin 2 Receptor," Proc. National Academic Science USA 86 (1989) 10029-10033.

Riechmann, L., et al., "Reshaping Human Anti-bodies for Therapy," Nature 332 (1988) 323-327.

Riechmann, L., et. al., "A Humanized Form of a CD4-Specific Monoclonal Antibody Exhibits Decreased Antigenicity and Prolonged Plasma Half-Life in Rhesus Monkeys While Retaining its Unique Biological and Antiviral Properties," *AIDS Res. and Human Retroviruses*, 1997, vol. 13 (11) pp. 933-943.

Root, M.J., et. al. "HIV-1 gp41 as a Target for Viral Entry Inhibition," *Curr. Pharma. Design* 2004, vol. 10, pp. 1805-1825.

Rossi, D. et. al., "The Biology of Chemokinds and Their Receptors," *Annu. Rev. Immunol.* (2000) vol. 18, pp. 217-242.

Samson, M., et. al., "Resistance to HIV-1 infection in Caucasian individuals bearing mutant alleles of the CCR-5 Chemokine Receptor Gene," Nature (1996) vol. 382, pp. 722-725.

Samson, M., et. al., "The Second Extracellular Loop of CCR5 Is the Major Determinant of Ligand Specificity," *J. Biological. Chem.* (1997) vol. 272 (40), pp. 24934-24941.

Schols, D., et. al., "HIV Co-receptors as Targets for Antiviral Therapy," *Curr. Top. Med. Chem.* (2004) vol. 4, pp. 883-893.

Schwarz, M.K., et al., "New Therapeutics that Modulate Chemokine Networks," *Nature Reviews Drug Discovery* 1 (2002) 347-358.

Shields, R.L., et al., "High Resolution mapping of the Binding Site on Human IgG1 for FcγRI, FcγRII, FcγRIII and FcRn and Design of IgG1 Variants with Improved Binding to the FcγR," *J. Biological Chemistry* 276 (2001) 6591-6604.

Shu, W. et. al., "Trimerization Specificity in HIV-1 gp41: Anaylsis with a GCN4 Leucine Zipper Model," *American Chem. Soc.* 1999, vol. 38, pp. 5378-5385.

Sia, S. K. et. al., "Short constrained Peptides that Inhibit HIV-1 Entry," *PNAS*, 2002, vol. 99 (23), pp. 14664-14669.

Spenlehauser, C. et al "A Luciferase-Reporter Gene-Expressing T-Cell Line Facilitates Neutralization and Drug-Sensitivity Assays that use Either R5 or X4 Strains of Human Immunodeficiency Virus Type 1," *Virology* 280 (2001) 292-300.

Strizki, J. M. et. al., "A Monoclonal Antibody (12G5) Directed against CxCr-4 Inhibits Infection with the Dual-Tropic Human Immunodeficiency Virus Type 1 Isolate HIV-1$_{89.6}$ but Not the T-Tropic Isolate HIV-1$_{HxB}$," *J. Virology*, 1997, vol. 71 (7), pp. 5678-5683.

Surman, S. et. al., "Localization of CD4$^+$ T Cell Epitope hotspots to Exposed Strand of HIV Envelope Glycoprotein suggests Structural Influences on Antigen Processing," *PNAS*, 2001, vol. 98 (8), pp. 4587-4592.

Tamamura, H. et. al., "The Therapeutic Potential of CXCR4 Antagonists in the Treatment of HIV Infection, Cancer Metastasis and Rheumatoid Arthritis," *Expert Opin. Ther. Targets* 2005, vol. 9 (6), pp. 1267-1282.

Thommesen, J.E. et al., "Lysine 322 in the human IgG3 $C_H2$ Domain is Crucial for Antibody Dependent Complement Activation," *Molecular Immunology* 37 (2000) 995-1004.

Trkola, A., et al., "A Cell Line-Based Neutralization Assay for Primary Human Immunodeficiency Virus Type 1 Isolates that use either the CCR5 or the CXCR4 Coreceptor," *Journal of Virology* 73 (1999) 8966-8974.

Vijayalakshmi, M.A. et. al., "Antibody Purification Methods," Applied Biochem. And Biotech. 1998, vol. 75, pp. 93-102.

* cited by examiner

US 7,951,920 B2

CONJUGATE OF AN ANTIBODY AGAINST CCR5 AND AN ANTIFUSOGENIC PEPTIDE

PRIORITY

This application claims priority under 35 USC §119 from European Application EP06017156.8 filed Aug. 17, 2006, and EP06020647.1 filed Sep. 29, 2006, both of which are incorporated herein by reference in full.

FIELD OF THE INVENTION

The present invention relates to a conjugate of an antibody against CCR5 and an anti-fusogenic peptide wherein one to eight antifusogenic peptides are each conjugated to one terminus of the heavy and/or light chains of an anti-CCR5 antibody. The antifusogenic peptides can be different, similar or identical on the amino acid level.

BACKGROUND OF THE INVENTION

The infection of cells by the human immunodeficiency virus (HIV) is effected by a process in which the membrane of the cells to be infected and the viral membrane are fused. A general scheme for this process is proposed: The viral envelope glycoprotein complex (gp120/gp41) interacts with a cell surface receptor located on the membrane of the cell to be infected. The binding of gp120 to, e.g., the CD4 receptor in combination with a co-receptor such as CCR-5 or CXCR-4 causes a change in the conformation of the gp120/gp41 complex. In consequence of this conformational change the gp41 protein is able to insert into the membrane of the target cell. This insertion is the beginning of the membrane fusion process. It is known that the amino acid sequence of the gp41 protein varies in different HIV strains because of naturally occurring polymorphisms. But the same domain architecture can be recognized, more precisely, a fusion signal, two heptad repeat domains (HR1, HR2) and a transmembrane domain (in N- to C-terminal direction). It is suggested that the fusion (or fusogenic) domain is participating in the insertion into and the disintegration of the cell membrane. The HR regions are built up of multiple stretches comprising seven amino acids ("heptad") (see e.g. W. Shu, et al., Biochem (1999) 38:5378-85). Beside the heptads one or more leucine zipper-like motifs are present. This composition accounts for the formation of a coiled coil structure of gp41 proteins and just as well of peptides derived from these domains. Coiled coils are in general oligomers consisting of two or more interacting helices. Peptides with amino acid sequences deduced from the HR1 or the HR2 domain of gp41 are effective in vitro and in vivo inhibitors of HIV uptake into cells (for example peptides see e.g. U.S. Pat. No. 5,464,933, U.S. Pat. No. 5,656,480, U.S. Pat. No. 6,258,782, U.S. Pat. No. 6,348,568, or U.S. Pat. No. 6,656,906). For example, T20 (also known as DP178, Fuzeon®, a HR2 peptide), T651 (U.S. Pat. No. 6,479,055), and T2635 (WO 2004/029074) are very potent inhibitors of HIV infection. It has been attempted to enhance the efficacy of HR2 derived peptides with, for example, amino acid substitutions or chemical crosslinking (S. K. Sia, et al., Proc. Natl. Acad. Sci. USA (2002) 99:14664-69; A. Otaka, et al., Angew. Chem. Int. Ed. (2002) 41:2937-40).

The conjugation of peptides to certain molecules can change their pharmacokinetic properties, e.g. the serum half-life of such peptide conjugates can be increased. Conjugations are reported, for example, for polyethylene glycol (PEG) and Interleukin-6 (EP 0 442 724), for PEG and Erythropoietin (WO 01/02017), for chimeric molecules comprising Endostatin and immunoglobulins (US 2005-008649), for secreted antibody based fusion proteins (US 2002-147311), for fusion polypeptides comprising albumin (US 2005-0100991; human serum albumin U.S. Pat. No. 5,876,969), for PEGylated polypeptides (US 2005-0114037), and for interferon fusions. Also described in the state of the art are immunotoxins comprising Gelonin and an antibody (WO 94/26910), modified transferrin-antibody fusion proteins (US 2003-0226155), antibody-cytokine fusion proteins (US 2003-0049227), and fusion proteins consisting of a peptide with immuno-stimulatory, membrane transport, or homophilic activity and an antibody (US 2003-0103984). In WO 2004/085505 long acting biologically active conjugates consisting of biologically active compounds chemically linked to macromolecules, are reported.

The co-receptor CCR5 is used by most HIV-1 primary isolates and is critical for the establishment and maintenance of infection. In addition, CCR5 function is dispensable for human health. A mutant CCR5 allele, "CCR5Δ32", encodes a truncated, non-functional protein (M. Samson, et al., Nature (1996) 382:722-25; M. Dean, et al., Science (1996) 273:1856-62). Individuals homozygous for the mutation lack CCR5 expression and are strongly protected from HIV-1 infection. They demonstrate no overt phenotype consequence and are highly resistant to M-tropic HIV infection, whereas heterozygote individuals present delayed disease progression (M. K. Schwarz and T. N. Wells, Nat. Rev. Drug Discov. (2002) 1:347-58). The lack of CCR5 is without apparent adverse consequences, probably because CCR5 is part of a highly redundant chemokine network as receptor for the α-chemokines MIP-1α, MIP-1β, and RANTES, which share many overlapping functions, and most of which have alternative receptors (D. Rossi and A. Zlotnik, Ann. Rev. Immunol. (2000) 18:217-42). The identification of CCR5 as an HIV-1 co-receptor was based on the ability of its ligands, MIP-1α, MIP-1β, and RANTES, to block infection by R5 but not R5X4 or X4 isolates (F. Cocchi, et al., Science (1995) 270:1811-15). CCR5 is also a receptor of the "cluster" chemokines, which are produced primarily during inflammatory responses and control the recruitment of neutrophils (CXC chemokines), macrophages and a subset of T cells (T helper Th1 and Th2 cells). Th1 responses are typically those involving cell-mediated immunity effective against viruses and tumors, proinflammatory responses responsible for killing intracellular parasites, and perpetuating autoimmune responses, for example, whereas Th2 responses are believed to be pivotal in allergies. Therefore, inhibitors of these chemokine receptors may be useful as immunomodulators. For Th1 responses, overactive responses are dampened, for example, in autoimmunity including rheumatoid arthritis, or, for Th2 responses, asthma attacks or allergic responses including atopic dermatitis are lessened (see e.g. D. Schols, Curr. Top. Med. Chem. (2004) 4:883-93; A. Mueller and P. G. Strange, Int. J. Biochem. Cell Biol. 36:35-38; W. M. Kazmierski et al., Curr. Drug Targets Infect. Disord. (2002) 2:265-78; T. Lehner, Trends Immunol. (2002) 23:347-51).

Antibodies against human CCR5 are e.g. PRO140 (W. C. Olson et al., J. Virol. (1999) 73:4145-55), and/or 2D7 (M. Samson et al., J. Biol. Chem. (1997) 272:24934-41). Additional antibodies are mentioned in US 2004-0043033, U.S. Pat. No. 6,610,834, US 2003-0228306, US 2003-0195348, US 2003-0166870, US 2003-0166024, US 2003-0165988, US 2003-0152913, US 2003-0100058, US 2003-0099645, US 2003-0049251, US 2003-0044411, US 2003-0003440, U.S. Pat. No. 6,528,625, US 2002-0147147, US 2002-0146415, US 2002-0106374, US 2002-0061834, US 2002-0048786, US 2001/0000241, EP 1 322 332, EP 1 263 791, EP 1 207 202, EP 1 161 456, EP 1 144 006, WO 2003/072766, WO 2003/066830, WO 2003/033666, WO 2002/083172, WO 02/22077, WO 01/58916, WO 01/58915, WO 01/43779, WO 01/42308, and EP 05007138.0.

Polyethylene glycol conjugates of antibodies against CCR5 are known from US 2003-0228306. US 2003-0215421 refers to chemokine-toxin conjugates. WO 01/43779 refers to conjugates of anti-CD4 antibodies and anti-CCR5 antibodies and to conjugates of anti-CD4 antibodies and an HIV-1 fusion inhibiting peptide. Conjugates of CCR5 antibodies and toxins are mentioned in EP 1 346 731.

SUMMARY OF THE INVENTION

The invention comprises a conjugate comprising one or more antifusogenic peptides and an anti-CCR5 antibody (mAb CCR5) characterized in that one to eight antifusogenic peptides are each conjugated to one terminus of the heavy and/or light chains of said anti-CCR5 antibody (a number of eight antifusogenic peptides per mAb CCR5 is only possible if the mAb CCR5 comprises eight termini, i.e. is composed e.g. of two heavy chains and two light chains; if the mAb CCR5 comprises a smaller number of C- and N-termini, e.g. as a scFv, the corresponding number of antifusogenic peptides possible at maximum in the conjugate is also reduced, i.e. it is reduced to less than eight).

Preferably the carboxy-terminal amino acid of an anti-CCR5 antibody chain is conjugated to the amino-terminal amino acid of the antifusogenic peptide or the carboxy-terminal amino acid of the antifusogenic peptide is conjugated to the amino-terminal amino acid of the antibody chain, preferably by a peptide bond with or without an intermediate linker.

Preferably the conjugate is characterized by the general formula mAb CCR5-[linker]$_m$-[antifusogenic peptide]$_n$ wherein m is independently for each antifusogenic peptide either 0 (i.e. a peptide bond between mAb CCR5 and antifusogenic peptide) or 1 (i.e. a linker between mAb CCR5 and antifusogenic peptide) and n is an integer of from 1 to 8.

A preferred conjugate of a heavy and/or light chain of mAb CCR5 and an antifusogenic peptide ("chain conjugate") is selected from the group consisting of:
(1) [antifusogenic peptide]-[linker]$_m$-[heavy chain]
(2) [heavy chain]-[linker]$_m$-[antifusogenic peptide]
(3) [antifusogenic peptide]-[linker]$_m$-[heavy chain]-[antifusogenic peptide]
(4) [antifusogenic peptide]-[linker]$_m$-[light chain]
(5) [light chain]-[linker]$_m$-[antifusogenic peptide]
(6) [antifusogenic peptide]-[linker]$_m$-[light chain]-[antifusogenic peptide]
(7) [antifusogenic peptide]-[linker]$_m$-[heavy chain]-[linker]$_m$-[antifusogenic peptide]
(8) [antifusogenic peptide]-[linker]$_m$-[light chain]-[linker]$_m$-[antifusogenic peptide]

wherein the linker can be the same or different in (within and between) said chain conjugates, wherein m is an integer of 1 or 0, and m can be independently the same or different in (within and between) said chain conjugates.

("Left side" of the peptide or mAb CCR5 chain means N-terminus, "right side" means C-terminus. In (1) therefore the C-terminus of the antifusogenic peptide is linked by a peptide bond or a linker to the N-terminus of the heavy chain of mAb CCR5).

Preferably the chain conjugates are assembled to conjugates according to the invention comprising a mAb CCR5 (e.g. consisting of two light chains and two heavy chains including the constant Fc domains, a scFv fragment, or a Fab fragment).

Especially preferred chain conjugates are (2), (3), (4), and (7). Especially preferred conjugates according to the invention comprise 2×[mAb CCR5 light chain] and 2×(2), 2×[mAb CCR5 light chain] and 2×(3), or 2×[mAb CCR5 heavy chain] and 2×(4), or 2×[mAb CCR5 light chain] and 2×(7). The heavy and/or light chain comprises preferably a constant region (Fc).

Preferably the conjugate is characterized in comprising a variable heavy chain domain consisting of an immunoglobulin framework and a CDR3 region selected from the group consisting of the heavy chain CDR3 sequences SEQ ID NO: 16, 17.

Preferably the conjugate is characterized in comprising a variable heavy chain domain consisting of an immunoglobulin framework and a CDR3 region selected from the group consisting of CDR3 sequences SEQ ID NO: 16, 17, a CDR2 region selected from the group consisting of CDR2 sequences SEQ ID NO: 13, 14, 15, and a CDR1 region selected from the group consisting of CDR1 sequences SEQ ID NO: 9, 10, 11, 12.

Preferably the conjugate is characterized in comprising a heavy chain variable domain selected from the group of heavy chain variable domains comprising SEQ ID NO: 1, 3, 5, and 7.

Preferably the conjugate is characterized in comprising a variable light chain domain consisting of an immunoglobulin framework and a CDR1 region selected from SEQ ID NO:18, 19, 20, a CDR2 region selected from SEQ ID NO:21, 22, 23, and a CDR3 region selected from SEQ ID NO:24, 25.

Preferably the conjugate is characterized in comprising as heavy chain CDRs the CDRs of SEQ ID NO:1 and as light chain CDRs the CDRs of SEQ ID NO:2, as heavy chain CDRs the CDRs of SEQ ID NO:3 and as light chain CDRs the CDRs of SEQ ID NO:4, as heavy chain CDRs the CDRs of SEQ ID NO:5 and as light chain CDRs the CDRs of SEQ ID NO:6, or as heavy chain CDRs the CDRs of SEQ ID NO:7 and as light chain CDRs the CDRs of SEQ ID NO:8.

Preferably the conjugate is characterized in comprising a variable heavy and light chain domain independently selected from the group consisting of a) the heavy chain ($V_H$) variable domain defined by amino acid sequence SEQ ID NO: 1 and the light chain ($V_L$) variable domain defined by amino acid sequence SEQ ID NO:2;
b) the heavy chain variable domain defined by amino acid sequence SEQ ID NO:3 and the light chain variable domain defined by amino acid sequence SEQ ID NO:4;
c) the heavy chain variable domain defined by amino acid sequence SEQ ID NO:5 and the light chain variable domain defined by amino acid sequence SEQ ID NO:6;
d) the heavy chain variable domain defined by amino acid sequence SEQ ID NO:7 and the light chain variable domain defined by amino acid sequence SEQ ID NO:8.

Preferably the conjugate is characterized in comprising the heavy chain ($V_H$) variable domain defined by amino acid sequence SEQ ID NO:1 and the light chain ($V_L$) variable domain defined by amino acid sequence SEQ ID NO:2; or the heavy chain variable domain defined by amino acid sequence SEQ ID NO:3 and the light chain variable domain defined by amino acid sequence SEQ ID NO:4; or the heavy chain variable domain defined by amino acid sequence SEQ ID NO:5 and the light chain variable domain defined by amino acid sequence SEQ ID NO:6; or the heavy chain variable domain defined by amino acid sequence SEQ ID NO:7 and the light chain variable domain defined by amino acid sequence SEQ ID NO:8; a linker selected from the group consisting of the amino acids glycine (G) and asparagine (N), the tripeptide GST, and SEQ ID NO:36-62; and an antifusogenic peptide selected from the group of peptides defined by SEQ ID NO:29 to 35.

Preferably the conjugate is characterized in comprising an antifusogenic peptide selected from the group of peptides comprising C34, T20, T1249, T651, T2635, N36, and DP107.

Preferably the conjugate is characterized in comprising an antifusogenic peptide at each C-terminus of the heavy chains or at each N-terminus of the light chains (two antifusogenic peptides). Preferably the conjugate is characterized in that it comprises an antifusogenic peptide at each C-terminus of the heavy chains and at each N-terminus of the light chains (four antifusogenic peptides).

Preferably the conjugate is characterized in comprising two light chain variable domains of SEQ ID NO:2, two conjugates of type (2) each comprising a heavy chain variable domain of SEQ ID NO:1, a linker of SEQ ID NO:40 and an antifusogenic peptide of SEQ ID NO:33, in comprising two light chain variable domains of SEQ ID NO:4, two conjugates of type (2) each comprising a heavy chain variable domain of SEQ ID NO:3, a linker of SEQ ID NO:40 and an antifusogenic peptide of SEQ ID NO:33, in comprising two light chain variable domains of SEQ ID NO:6, two conjugates of type (2) each comprising a heavy chain variable domain of SEQ ID NO:5, a linker of SEQ ID NO:40 and an antifusogenic peptide of SEQ ID NO:33, or in comprising two light chain variable domains of SEQ ID NO:8, two conjugates of type (2) each comprising a heavy chain variable domain of SEQ ID NO:7, a linker of SEQ ID NO:40 and an antifusogenic peptide of SEQ ID NO:33.

Preferably the conjugate is characterized in that said anti-CCR5 antibody is of IgG1 subclass. It is also preferred, that said anti-CCR5 antibody is of IgG4 subclass, or of IgG1 or IgG2 subclass, with a mutation in amino acid position S228, L234, L235, and/or D265, and/or contains the PVA236 mutation. Preferably the conjugate is characterized in that said anti-CCR5 antibody of IgG4 subclass has a S228P mutation and said anti-CCR5 antibody of IgG1 subclass has L234A and L235A mutations.

The invention comprises a method for the production of a conjugate according to the invention, characterized in that the method comprises
a) cultivating a cell containing one or more plasmids containing one or more nucleic acid molecules encoding a conjugate according to the invention under conditions suitable for the expression of the conjugate,
b) recovering the conjugate from the cell or the supernatant.

In one embodiment are the genes encoding the light and heavy chains of mAb CCR5 with or without linked antifusogenic peptide located on the same expression vector or on different expression vectors.

The invention comprises a pharmaceutical composition, containing a conjugate according to the invention, together with a pharmaceutically acceptable excipient or carrier.

The invention comprises the use of a conjugate according to the invention for the manufacture of a medicament for the treatment of viral infections. Preferably the use is characterized in that the viral infection is a HIV infection.

The invention comprises the use of a conjugate according to the invention for the treatment of a patient in need of an antiviral treatment, preferably an anti HIV treatment.

DESCRIPTION OF THE INVENTION

The current invention reports a conjugate comprising one or more antifusogenic peptides and an anti-CCR5 antibody (mAb CCR5) characterized in that one to eight antifusogenic peptides are each conjugated to one terminus of the heavy and/or light chains of said anti-CCR5 antibody. A number of eight antifusogenic peptides per mAb CCR5 is only possible if the mAb CCR5 comprises eight termini, i.e. is composed e.g. of two heavy chains and two light chains. If the mAb CCR5 comprises a smaller number of C- and N-termini, e.g. as a scFv, the corresponding number of antifusogenic peptides possible at maximum in the conjugate is also reduced, i.e. it is reduced to less than eight.

An "antifusogenic peptide" is a peptide which inhibits events associated with membrane fusion or the membrane fusion event itself, including, among other things, the inhibition of infection of uninfected cells by a virus due to membrane fusion. These antifusogenic peptides are preferably linear peptides. For example, they can be derived from the gp41 ectodomain, e.g. such as DP107, DP178. Examples of such peptides can be found in U.S. Pat. No. 5,464,933, U.S. Pat. No. 5,656,480, U.S. Pat. No. 6,013,263, U.S. Pat. No. 6,017,536, U.S. Pat. No. 6,020,459, U.S. Pat. No. 6,093,794, U.S. Pat. No. 6,060,065, U.S. Pat. No. 6,258,782, U.S. Pat. No. 6,348,568, U.S. Pat. No. 6,479,055, U.S. Pat. No. 6,656,906, WO 1996/19495, WO 1996/40191, WO 1999/59615, WO 2000/69902, and WO 2005/067960. For example, the amino acid sequences of such peptides comprise or can be selected from the group of SEQ ID NO: 1 to 10 of U.S. Pat. No. 5,464,933; SEQ ID NO:1 to 15 of U.S. Pat. No. 5,656,480; SEQ ID NO: 1 to 10 and 16 to 83 of U.S. Pat. No. 6,013,263; SEQ ID NO: 1 to 10, 20 to 83 and 139 to 149 of U.S. Pat. No. 6,017,536; SEQ ID NO:1 to 10, 17 to 83 and 210 to 214 of U.S. Pat. No. 6,093,794; SEQ ID NO:1 to 10, 16 to 83 and 210 to 211 of U.S. Pat. No. 6,060,065; SEQ ID NO:1286 and 1310 of U.S. Pat. No. 6,258,782; SEQ ID NO:1129, 1278-1309, 1311 and 1433 of U.S. Pat. No. 6,348,568; SEQ ID NO:1 to 10 and 210 to 238 of U.S. Pat. No. 6,479,055; SEQ ID NO:1 to 171, 173 to 216, 218 to 219, 222 to 228, 231, 233 to 366, 372 to 398, 400 to 456, 458 to 498, 500 to 570, 572 to 620, 622 to 651, 653 to 736, 739 to 785, 787 to 811, 813 to 823, 825, 827 to 863, 865 to 875, 877 to 883, 885, 887 to 890, 892 to 981, 986 to 999, 1001 to 1003, 1006 to 1018, 1022 to 1024, 1026 to 1028, 1030 to 1032, 1037 to 1076, 1078 to 1079, 1082 to 1117, 1120 to 1176, 1179 to 1213, 1218 to 1223, 1227 to 1237, 1244 to 1245, 1256 to 1268, 1271 to 1275, 1277, 1345 to 1348, 1350 to 1362, 1364, 1366, 1368, 1370, 1372, 1374 to 1376, 1378 to 1379, 1381 to 1385, 1412 to 1417, 1421 to 1426, 1428 to 1430, 1432, 1439 to 1542, 1670 to 1682, 1684 to 1709, 1712 to 1719, 1721 to 1753, 1755 to 1757 of U.S. Pat. No. 6,656,906; or SEQ ID NO:5 to 95 of WO 2005/067960. The antifusogenic peptide has an amino acid sequence comprising of from 5 to 100 amino acids, preferably of from 10 to 75 amino acids and more preferred of from 15 to 50 amino acids. Especially preferred antifusogenic peptides are C-34, T-20, T-1249, T-651, T-2635, N-36, (M. J. Root et al., *Curr. Pharm. Des.* (2004) 10:1805-25) and DP-107 (C. Wild et al., *Proc. Natl. Acad. Sci. USA* (1994) 91:12676-80). One embodiment comprises the conjugate according to the invention one or more antifusogenic peptides and an anti-CCR5 antibody (mAb CCR5) wherein i) said antifusogenic peptides are linear peptides with an amino acid sequence of from 5 to 100 amino acids, and ii) one to eight antifusogenic peptides are each conjugated to one terminus of the heavy and/or light chains of said anti-CCR5 antibody. Another embodiment comprises the conjugate according to the invention having one or more antifusogenic peptides and an anti-CCR5 antibody (mAb CCR5) wherein i) said antifusogenic peptides are derived from the gp41 ectodomain, and ii) one to eight antifusogenic peptides are each conjugated to one terminus of the heavy and/or light chains of said anti-CCR5 antibody. The term "gp41 ectodomain" denotes the amino acid sequence starting with amino acid position 561 and ending with amino acid position 620 of HIV-1 gp 160 or starting with amino acid position 50 and ending with amino acid position 109 of HIV-1 gp41 (SEQ ID NO:66) (see also e.g. S. Bar and M. J. Alizon, *Virol*. (2004) 78:811-20).

The term "antibody" encompasses the various forms of antibody structures including whole antibodies and antibody fragments. The antibody according to the invention is preferably a human antibody, a humanized antibody, a chimeric antibody, a T cell antigen depleted antibody (WO 98/33523, WO 98/52976, and WO 00/34317). Genetic engineering of antibodies is e.g. described in S. L. Morrison et al., *Proc. Natl. Acad. Sci. USA* (1984) 81:6851-55; U.S. Pat. Nos. 5,202,238 and 5,204,244; L. Riechmann et al., *Nature* (1988) 332:323-27; M. S. Neuberger et al., *Nature* (1985) 314:268-70; N. Lonberg, *Nat. Biotechnol*. (2005) 23:1117-25.

"Antibody fragments" comprise a portion of a full length anti-CCR5 antibody, preferably the variable domains thereof or at least the antigen binding portion thereof. Examples of anti-body fragments are e.g. single-chain antibody molecules (scFv), Fab, F(ab)$_2$ fragments, and the like as long as they retain the characteristics of an anti-CCR5 antibody. ScFv antibodies are, e.g., described in J. S. Huston, *Meth. Enzymol*. (1991) 203:46-88. Huston also describes linkers and methods for linking of polypeptides useful for the present invention.

"CCR5" means human CCR5 as described, e.g., in M. Oppermann, *Cell Signal*. (2004) 16:1201-10 and SwissProt P51681. The terms "antibody binding to CCR5", "anti-CCR5 antibody", or "mAb CCR5", which are used interchangeably within this application, mean an antibody specifically binding to CCR5 and preferably inhibiting HIV fusion with a target cell. Binding can be tested in a cell based in vitro ELISA assay (CCR5 expressing CHO cells). Binding is found if the antibody causes an S/N (signal/noise) ratio of 5 or more, preferably 10 or more at an antibody concentration of 100 ng/ml. The term "inhibiting HIV fusion with a target cell" refers to inhibiting HIV fusion with a target cell measured in an assay comprising contacting said target cell (e.g. PBMC) with the virus in the presence of the antibody in a concentration effective to inhibit membrane fusion between the virus and said cell and measuring e.g. luciferase reporter gene activity or the HIV p24 antigen concentration. The term "membrane fusion" refers to fusion between a first cell coexpressing CCR5 and CD4 polypeptides and a second cell or virus expressing an HIV env protein. Membrane fusion is determined by genetically engineered cells and/or viruses by a reporter gene assay (e.g. by luciferase reporter gene assay).

Preferred anti-CCR5 antibodies are mentioned in US 2004-0043033, U.S. Pat. No. 6,610,834, US 2003-0228306, US 2003-0195348, US 2003-0166870, US 2003-0166024, US 2003-0165988, US 2003-0152913, US 2003-0100058, US 2003-0099645, US 2003-0049251, US 2003-0044411, US 2003-0003440, U.S. Pat. No. 6,528,625, US 2002-0147147, US 2002-0146415, US 2002-0106374, US 2002-0061834, US 2002-0048786, US 2001/0000241, EP 1 322 332, EP 1 263 791, EP 1 207 202, EP 1 161 456, EP 1 144 006, WO 2003/072766, WO 2003/066830, WO 2003/033666, WO 2002/083172, WO 02/22077, WO 01/58916, WO 01/58915, WO 01/43779, WO 01/42308, and WO 2006/103100. Especially preferred anti-CCR5 antibodies are described in WO 2006/103100. An especially preferred anti-CCR5 antibody is characterized in that the antibody comprises a variable heavy chain domain consisting of an immunoglobulin framework and a CDR3 region selected from the group consisting of the heavy chain CDR3 sequences SEQ ID NO:16, 17. A further preferred antibody comprises a variable heavy chain region consisting of an immunoglobulin framework and a CDR3 region selected from the group consisting of CDR3 sequences SEQ ID NO: 16, 17, a CDR2 region selected from the group consisting of CDR2 sequences SEQ ID NO:13, 14, 15, and a CDR1 region selected from the group consisting of CDR1 sequences SEQ ID NO:9, 10, 11, 12. Preferred heavy chain variable domains are shown in SEQ ID NO:1, 3, 5, 7. A preferred anti-CCR5 antibody comprises in addition a variable light chain domain consisting of an immunoglobulin framework and a CDR1 region selected from the group consisting of CDR1 sequences SEQ ID NO:18, 19, 20, a CDR2 region selected from the group consisting of CDR2 sequences SEQ ID NO:21, 22, 23, and a CDR3 region selected from the group of CDR3 sequences SEQ ID NO:24, 25. The anti-CCR5 antibody is preferably characterized in containing as heavy chain CDRs the CDRs of SEQ ID NO: 1 and as light chain CDRs the CDRs of SEQ ID NO:2, as heavy chain CDRs the CDRs of SEQ ID NO:3 and as light chain CDRs the CDRs of SEQ ID NO:4, as heavy chain CDRs the CDRs of SEQ ID NO:5 and as light chain CDRs the CDRs of SEQ ID NO:6, or as heavy chain CDRs the CDRs of SEQ ID NO:7 and as light chain CDRs the CDRs of SEQ ID NO:8.

CDR sequences can be determined according to the standard definition of E. A. Kabat et al., Sequences of Proteins of Immunological Interest, 5th ed., Public Health Service, National Institutes of Health, Bethesda, Md. (1991). CDRs of SEQ ID NO: 1-8 are shown in SEQ ID NO:9-25.

The anti-CCR5 antibody comprises preferably a variable heavy and light chain domain independently selected from the group consisting of a) the heavy chain ($V_H$) variable domain defined by amino acid sequence SEQ ID NO: 1 and the light chain ($V_L$) variable domain defined by SEQ ID NO:2;

b) the heavy chain variable domain defined by amino acid sequence SEQ ID NO:3 and the light chain variable domain defined by SEQ ID NO:4;

c) the heavy chain variable domain defined by amino acid sequence SEQ ID NO:5 and the light chain variable domain defined by SEQ ID NO:6;

d) the heavy chain variable domain defined by amino acid sequence SEQ ID NO:7 and the light chain variable domain defined by SEQ ID NO:8.

The antibody used in the conjugate according to the invention is preferably characterized in that the constant domains are of human origin. Such constant domains are well known in the state of the art and, e.g., described by Kabat (see e.g. G. Johnson and T. T. Wu, *Nucleic Acids Res*. (2000) 28:214-18). For example, a useful human IgG1 heavy chain constant region ($C_H1$-Hinge-$C_H2$-$C_H3$) comprises an amino acid sequence independently selected from the group consisting of SEQ ID NO:26, 27. For example, a useful human kappa (κ) light chain constant domain comprises an amino acid sequence of a kappa light chain constant domain (κ light chain constant domain, $C_L$) of SEQ ID NO:28. It is further preferred that the antibody's variable domains are of mouse origin and comprises the antibody variable domain sequence frame of a mouse antibody according to Kabat (see e.g. G. Johnson and T. T. Wu, supra).

A preferred anti-CCR5 antibody shows a binding to the same epitope(s) of CCR5 as does an antibody selected from the group consisting of the antibodies A to E or is inhibited in binding to CCR5 by antibodies A to E due to steric hindrance of binding or competitive binding. Epitope binding is investigated by using alanine scanning according to the method described by W. C. Olson et al. (*J. Virol*. (1999) 73:4145-55)

for epitope mapping. A signal reduction of 75% or more shows that the mutated amino acid(s) contribute to the epitope recognized by said antibody. Binding of the antibody to the same epitope is found, if the amino acids contributing to the epitope are recognized by the investigated antibody and antibody A, B, C, D, or E. Antibody C, which shows lower $IC_{50}$ values than antibody 2D7 in HIV assays, binds to an epitope including amino acids on the ECL2 domain of CCR5 (B. Lee et al., *J. Biol. Chem.* (1999) 274:9617-26) which is different from the epitope recognized by antibody 2D7 (2D7 binds to amino acids K171 and E172 of ECL2A but not to ECL2B amino acids 184-189). Epitope binding for antibody C is found to be 20% for CCR5 mutant K171A or E172A (glu 172 is mutated to ala). 100% epitope binding is defined for wild-type CCR5. A further preferred anti-CCR5 antibody binds to the same epitope as antibody C binds.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. Preferably an antibody according to the invention binds specifically to native but not to denatured CCR5. Such an antibody comprises preferably heavy chain CDR3 of SEQ ID NO: 17, and preferably in addition heavy chain CDRs selected from the group of CDRs of SEQ ID NO:10, 11, 12, 14 and/or 15. Preferably such an antibody is antibody B, C, D, or E, or comprises the variable domains of antibody B, C, D, or E. Preferably an antibody binding to denatured CCR5 is antibody A or comprises the variable domains of antibody A.

The term "variable domain" (variable domain of a light chain ($V_L$), variable domain of a heavy chain ($V_H$)) as used herein denotes each domain of the pair of light and heavy chain domains which is involved directly in the binding of the antibody to the antigen. The variable domains of the light and heavy chain have the same general structure, i.e. they possess an "immunoglobulin framework", and each domain comprises four "framework regions" (FR), whose sequences are widely conserved, connected by three "hypervariable regions" (or "complementarity determining regions", CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "antigen-binding portion of an antibody" or "antigen-binding site of an antibody" when used herein refer to the amino acid residues of an antibody which are responsible for antigen-binding. The antigen-binding site of an antibody comprises amino acid residues from the "complementarity determining regions" or "CDRs". "Framework" or "FR" regions are those variable domain regions other than the hypervariable region residues as herein defined. Therefore, the light and heavy chain variable domains of an antibody comprise from N- to C-terminus the regions FR1, CDR1, FR2, CDR2, FR3, CDR3, and FR4 (immunoglobulin framework). Especially, the CDR3 region of the heavy chain is the region which contributes most to antigen binding and defines the antibody. Preferably the antibody according to the invention is characterized by comprising in its heavy chain variable domain the CDR3 sequence of SEQ ID NO:16 or SEQ ID NO:17. Complementarity determining (CDR) and framework (FR) regions are determined according to the standard definition of E. A. Kabat et al., Sequences of Proteins of Immunological Interest, 5th ed., Public Health Service, National Institutes of Health, Bethesda, Md. (1991).

The "Fc part" of an anti-CCR5 antibody is not involved directly in binding to CCR5, but exhibit various effector functions. Depending on the amino acid sequence of the constant region of their heavy chains, antibodies or immunoglobulins are divided in the classes: IgA, IgD, IgE, IgG, and IgM, and several of these may be further divided into subclasses (isotypes), e.g. IgG1, IgG2, IgG3, and IgG4, IgA1 and IgA2. According to the heavy chain constant regions the different classes of immunoglobulins are called α, δ, ε, γ, and μ, respectively. The antibodies according to the invention are preferably of IgG type. An "Fc part of an antibody" is a term well known to the skilled artisan and defined on basis of papain cleavage of antibodies. The antibodies according to the invention contain as Fc part a human Fc part or an Fc part derived from human origin. In a further embodiment of the invention the Fc part is either an Fc part of a human antibody of the subclass IgG4 or an Fc part of a human antibody of the subclass IgG1, IgG2, or IgG3, which is modified in such a way that no Fcγ receptor (e.g. FcγRIIIa) binding and/or no C1q binding as defined below can be detected. Preferably the Fc part is a human Fc part and especially preferred either from human IgG4 subclass or a mutated Fc part from human IgG1 subclass. Further preferred are Fc parts from human IgG1 subclass with mutations L234A and L235A. Further preferred are Fc parts shown in SEQ ID NO: 26, SEQ ID NO: 27, SEQ ID NO: 26 with mutations L234A and L235A, SEQ ID NO: 27 with mutation S228P. While IgG4 shows reduced Fcγ receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which if altered provide also reduced Fcγ receptor binding (R. L. Shields et al., *J. Biol. Chem.* (2001) 276:6591-604; J. Lund et al., *FASEB J.* (1995) 9:115-19; A. Morgan et al., *Immunol.* (1995) 86:319-24; EP 0 307 434). Preferably an antibody according to the invention is in regard to Fcγ receptor binding of IgG4 subclass or of IgG1 or IgG2 subclass, with a mutation in L234, L235, and/or D265, and/or contains the PVA236 mutation. Preferred are the mutations S228P, L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA). Especially preferred are the mutations S228P of IgG4, and L234A and L235A of IgG1. The Fc part of an antibody is directly involved in ADCC (antibody-dependent cell-mediated cytotoxicity) and CDC (complement-dependent cytotoxicity). Complement activation (CDC) is initiated by binding of complement factor C1q to the Fc part of most IgG antibody subclasses. Binding of C1q to an antibody is caused by defined protein-protein interactions at the so called binding site. Such Fc part binding sites are known in the state of the art and described e.g. by T. J. Lukas et al., *J. Immunol.* (1981) 127:2555-60; R. Brunhouse and J. J. Cebra, *Mol. Immunol.* (1979) 16: 907-17; D. R. Burton et al., *Nature* (1980) 288:338-44; J. E. Thommesen et al., *Mol. Immunol.* (2000) 37:995-1004; E. E. Idusogie et al., *J. Immunol.* (2000) 164:4178-84; M. Hezareh et al., *J. Virol.* (2001) 75:12161-68; A. Morgan et al., *Immunol.* (1995) 86:319-24; and EP 0 307 434. Such Fc part binding sites are, e.g., characterized by the amino acids L234, L235, D270, N297, E318, K320, K322, P331, and P329 (numbering according to EU index of Kabat).

Antibodies of subclass IgG1, IgG2, and IgG3 usually show complement activation including C1q and C3 binding, whereas IgG4 does not activate the complement system and does not bind C1q and C3. An anti-CCR5 antibody which does not bind Fcγ receptor and/or complement factor C1q does not elicit antibody-dependent cellular cytotoxicity (ADCC) and/or complement dependent cytotoxicity (CDC). Preferably, this antibody is characterized in that it binds CCR5, contains an Fc part derived from human origin, and does not bind Fcγ receptors and/or complement factor C1q. More preferably, this antibody is a human, or humanized, or a T-cell antigen depleted antibody. C1q binding can be measured according to Idusogie, E. E., et al., *J. Immunol.* 164 (2000) 4178-4184. No "C1q binding" is found if in such an assay the optical density (OD) at 492-405 nm is for the test antibody lower than 15% of the value for human C1q binding of the unmodified wild-type antibody Fc part at an antibody concentration of 8 μg/ml. ADCC can be measured as binding of the antibody to human FcγRIIIa on human NK cells. Binding is determined at an antibody concentration of 20 μg/ml. "No Fcγ receptor binding" or "no ADCC" means a binding of up to 30% to human FcγRIIIa on human NK cells at an antibody concentration of 20 μg/ml compared to the binding of the same antibody as human IgG1 (SEQ ID NO:26).

An antibody used in a conjugate according to the invention include, in addition, such antibodies having "conservative sequence modifications" (variant antibodies), which are amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), non-polar side chains (e.g. alanine, valine, leucine, isoleucine, proline, phenylalanine, methionine), beta-branched side chains (e.g. threonine, valine, isoleucine), and aromatic side chains (e.g. tyrosine, phenylalanine, tryptophan, histidine). Thus, a predicted nonessential amino acid residue in a human anti-CCR5 antibody can be preferably replaced with another amino acid residue from the same side chain family. A "variant" anti-CCR5 antibody, refers therefore herein to a molecule which differs in amino acid sequence from a "parent" anti-CCR5 antibody's amino acid sequence by up to ten, preferably from about two to about five, additions, deletions, and/or substitutions in one or more of the variable domain regions of the parent antibody outside the heavy chain CDR3 region. Each other heavy chain CDR region comprises at maximum one single amino acid addition, deletion, and/or substitution. The invention comprises a method of modifying the CDR amino acid sequence of a parent antibody binding to CCR5, characterized in selecting a heavy chain variable domain from the group of heavy chain variable domains consisting of SEQ ID NO: 1, 3, 5, 7, and/or a light chain variable domain from the group of light chain variable domains consisting of SEQ ID NO:2, 4, 6, 8, providing a nucleic acid encoding said initial variable domain amino acid sequence, modifying said nucleic acid in that one amino acid is modified in heavy chain CDR1, one amino acid is modified in heavy chain CDR2, 1-3 amino acid are modified in light chain CDR1, 1-3 amino acids are modified in light chain CDR2, and/or 1-3 amino acids are modified in light chain CDR3, expressing and incorporating said modified variable domain(s) amino acid sequence in an antibody structure, measuring whether said antibody binds to CCR5 and selecting said modified variable domain(s)/CDR(s) if the antibody binds to CCR5. Preferably such modifications are conservative sequence modifications. Amino acid sequence modifications can be performed by mutagenesis based on molecular modeling as described by L. Riechmann et al., *Nature* (1988) 332:323-27, and C. Queen et al., *Proc. Natl. Acad. Sci. USA* (1989) 86:10029-33.

The term "linker" or "peptidic linker" as used within this application denotes peptide linkers of natural and/or synthetic origin. They are building up of a linear amino acid chain wherein the 20 naturally occurring amino acids are the monomeric building blocks. The chain has a length of from 1 to 50 amino acids, preferred between 1 and 28 amino acids, especially preferred between 3 and 25 amino acids. The linker may contain repetitive amino acid sequences or sequences of naturally occurring polypeptides, such as polypeptides with a hinge-function. The linker has the function to ensure that a peptide conjugated to an anti-CCR5 antibody can perform its biological activity by allowing the peptide to fold correctly and to be presented properly. Preferably the linker is a "synthetic peptidic linker" that is designated to be rich in glycine, glutamine, and/or serine residues. These residues are arranged e.g. in small repetitive units of up to five amino acids. This small repetitive unit may be repeated for two to five times to form a multimeric unit. At the amino- and/or carboxy-terminal ends of the multimeric unit up to six additional arbitrary, naturally occurring amino acids may be added. Other synthetic peptidic linkers are composed of a single amino acid, that is repeated between 10 to 20 times. At each of the amino- and/or carboxy-terminal end up to six additional arbitrary, naturally occurring amino acids may be present. Preferred linkers are shown in Table 2. Especially preferred are linkers $[GQ_4]_3$GNN (SEQ ID NO:40), LSLSPGK (SEQ ID NO:36), LSPNRGEC (SEQ ID NO:37), LSLSGG (SEQ ID NO:61), LSLSPGG (SEQ ID NO:62). All peptidic linkers can be encoded by a nucleic acid molecule and therefore can be recombinantly expressed. As the linkers are themselves peptides, the antifusogenic peptide is connected to the linker via a peptide bond that is formed between two amino acids. The peptidic linker is introduced between the antifusogenic peptide and the anti-CCR5 antibody chain to which the antifusogenic peptide is to be conjugated. Therefore two or three, respectively, possible sequences (in amino- to carboxy-terminal direction) exist: a) antifusogenic peptide-peptidic linker-anti-CCR5 antibody polypeptide chain, or b) anti-CCR5 antibody polypeptide chain-peptidic linker-antifusogenic peptide, or c) antifusogenic peptide-peptidic linker-anti-CCR5 antibody polypeptide chain-peptidic linker-antifusogenic peptide.

In one embodiment of the invention the conjugate is characterized in comprising i) the heavy chain ($V_H$) variable domain defined by amino acid sequence SEQ ID NO:1 and the light chain ($V_L$) variable domain defined by SEQ ID NO:2; or the heavy chain variable domain defined by amino acid sequence SEQ ID NO:3 and the light chain variable domain defined by SEQ ID NO:4; or the heavy chain variable domain defined by amino acid sequence SEQ ID NO:5 and the light chain variable domain defined by SEQ ID NO:6; or the heavy chain variable domain defined by amino acid sequence SEQ ID NO:7 and the light chain variable domain defined by SEQ ID NO:8; ii) a linker selected from the group consisting of the amino acids glycine (G) and asparagine (N), the tripeptide GST, and SEQ ID NO:36-62; and iii) an antifusogenic peptide selected from the group of peptides defined by SEQ ID NO:29 to 35.

A preferred conjugate of a heavy and/or light chain of mAb CCR5 and an antifusogenic peptide(s) ("chain conjugate") is selected from the group consisting of the conjugates (1) [antifusogenic peptide]-[linker]$_m$-[heavy chain], (2) [heavy chain]-[linker]$_m$-[antifusogenic peptide], (3) [antifusogenic peptide]-[linker]$_m$-[heavy chain]-[antifusogenic peptide], (4) [antifusogenic peptide]-[linker]$_m$-[light chain], (5) [light chain]-[linker]$_m$-[antifusogenic peptide], (6) [antifusogenic peptide]-[linker]$_m$-[light chain]-[antifusogenic peptide], (7) [antifusogenic peptide]-[linker]$_m$-[heavy chain]-[linker]$_m$-[antifusogenic peptide], (8) [antifusogenic peptide]-[linker]$_m$-[light chain]-[linker]$_m$-[antifusogenic peptide], wherein the linker can be the same or different both within and between said chain conjugates, wherein m is an integer of 1 or 0, and m can be independently the same or different both within and between said conjugates. For example in a conjugate comprising a chain conjugate (7) and a mAb CCR5 light chain the two linkers in chain conjugate (7) can be the same, i.e. have the same amino acid sequence and length, or can be different, i.e. have different amino acid sequences and/or lengths, or one or both can be absent. For example in a conjugate comprising chain conjugates (2) and (4) the linker contained in chain conjugate (2) and the linker contained in chain conjugate (4) can be the same, i.e. have the same amino acid sequence and length, or can be different, i.e. have different amino acid sequences and/or lengths, or one or both can be absent. In the chain conjugates the linker(s) can be present (m=1) or absent (m=0). Preferred chain conjugates are the chain conjugates (2), (3), (4), and (7). One embodiment of the current invention is a conjugate comprising 2×[mAb CCR5 light chain] and 2× chain conjugate (2). This conjugate comprises two not conjugate anti-CCR5 antibody light chains and two anti-CCR5 antibody heavy chains conjugated via the C-terminus to the N-terminus of an antifusogenic peptide, optionally with an intermediate linker. Another embodiment of the current invention is a conjugate comprising two mAb CCR5 light chains and two chain conjugates (3). Still another embodiment is a conjugate comprising two mAb CCR5 heavy chains and two chain conjugates (4). A further embodiment of the current invention is a conjugate comprising two mAb CCR5 light chains and two chain conjugates (7). The heavy and/or light chain comprises preferably a constant region (Fc).

The invention further provides a method for the manufacture of a pharmaceutical composition comprising an effective amount of a conjugate according to the invention together with a pharmaceutically acceptable carrier and the use of the conjugate according to the invention for such a method.

The invention further provides the use of a conjugate according to the invention in an effective amount for the manufacture of a pharmaceutical agent, preferably together with a pharmaceutically acceptable carrier, for the treatment of a patient suffering from AIDS.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

Methods and techniques known to a person skilled in the art, which are useful for carrying out the current invention, are described e.g. in F. M. Ausubel, ed., Current Protocols in Molecular Biology, Volumes I to III (1997), Wiley and Sons; Sambrook et al., Molecular Cloning: A Laboratory Manual, Second Edition, Cold Spring Harbor Laboratory Press, Cold Spring Harbor, N.Y. (1989).

In the conjugates according to the invention the carboxy-terminal amino acid of an anti-CCR5 antibody chain is conjugated via a peptide bond to the amino-terminal amino acid of the antifusogenic peptide or the carboxy-terminal amino acid of the antifusogenic peptide is conjugated via a peptide bond to the amino-terminal amino acid of an anti-CCR5 antibody chain. In one embodiment an intermediate linker is present between the antifusogenic peptide and the anti-CCR5 antibody chain. Thus, the conjugate according to the invention is characterized by the general formula mAb CCR5-[linker]$_m$-[antifusogenic peptide]$_n$ wherein m is independently for each antifusogenic peptide either 0 (i.e. a direct peptide bond between mAb CCR5 and the antifusogenic peptide) or 1 (i.e. a linker is present between mAb CCR5 and antifusogenic peptide) and n is an integer of from 1 to 8. In one embodiment n is an integer of from 2 to 8. In another embodiment n is an integer of from 2 to 4. In another embodiment n is an integer of 2 or 4. One embodiment of the invention comprises a conjugate characterized in comprising an antifusogenic peptide at each C-terminus of the heavy chains or at each N-terminus of the light chains of the anti-CCR5 antibody. In this embodiment two antifusogenic peptides are conjugated to one anti-CCR5 antibody. In an other embodiment is the conjugate characterized by comprising an antifusogenic peptide at each C-terminus of the heavy chains and at each N-terminus of the light chains. In this embodiment four antifusogenic peptides are conjugated to one anti-CCR5 antibody.

The antifusogenic peptide which is introduced at a terminus of a mAb CCR5 heavy and/or light chain(s) is small of size compared to the mAb CCR5. For example, the smallest immunoglobulins, immunoglobulins of class G, have a molecular weight of approximately 150 kDa; an antifusogenic peptide has preferably a size (molecular weight) of less than 12.5 kDa, which is equivalent to about 100 amino acids, in general less than 7.5 kDa, which is equivalent to about 60 amino acids. The antifusogenic peptide has an amino acid sequence of from 5 to 100 amino acid residues, preferably of from 10 to 75 amino acid residues, more preferably of from 15 to 50 amino acid residues. The conjugates of the current invention are useful for pharmaceutical, therapeutical, or diagnostical applications. The number of antifusogenic peptides, which can be conjugated to mAb CCR5 heavy and/or light chain(s), is from one to the combined number of amino- and carboxy-termini of the anti-CCR5 antibody polypeptide chains. As the current invention encompasses different anti-CCR5 antibodies the number of antifusogenic peptides can vary. In case of an anti-CCR5 antibody comprising two heavy and two light chains the combined number of amino-termini (N-termini) and carboxy-termini (C-termini) is eight, which is at the same time the totaling maximum number of conjugated antifusogenic peptides; in case e.g. of an anti-CCR5 antibody fragment such as a single chain antibody (scFv) the combined number of termini and therefore the maximum number of conjugatable antifusogenic peptides is two. If a single antifusogenic peptide is conjugated to mAb CCR5, the peptide can occupy any one of the termini of the anti-CCR5 antibody chains. Likewise, if the maximum possible number of peptides is conjugated to mAb CCR5, all termini are occupied by a single peptide. If the number of peptides, which are conjugated to mAb CCR5, is smaller than the maximum possible number, different distributions of the peptides at the termini of the anti-CCR5 antibody chains are possible. For example, if four peptides are conjugated to an immunoglobulin of the G or E class, five different combinations are possible (see Table 1). In two combinations all termini of one kind, i.e. all four amino-termini or all four carboxy-termini of the anti-CCR5 antibody chains, are each conjugated to one single antifusogenic peptide. The other termini are not conjugated. This results in one embodiment in an allocation of the modifications/conjugations in one area of the anti-CCR5 antibody. In the other cases the polypeptides are conjugated to a number of both termini. Within these combinations the conjugated peptides are allocated to different areas of the anti-CCR5 antibody. In either case the sum of conjugated termini is four.

TABLE 1

Possible combination for the conjugation of four peptides to the termini of an anti-CCR5 antibody composed of four polypeptide chains.

| number of occupied amino-termini | number of occupied carboxy-termini | total number of occupied termini |
| --- | --- | --- |
| 4 | 0 | 4 |
| 3 | 1 | 4 |
| 2 | 2 | 4 |
| 1 | 3 | 4 |
| 0 | 4 | 4 |

The current invention preferably comprises conjugates in which at least two of the termini are conjugated to an antifusogenic peptide. The amino acid sequences of the antifusogenic peptides can be different, similar or identical. In one embodiment the amino acid sequence identity is in the range of from 90% to less than 100%; these amino acid sequences and the corresponding peptides are defined as similar. In a preferred embodiment the antifusogenic peptides are identical, i.e. have an amino acid identity of 100%.

The present invention comprises a conjugate comprising one or more antifusogenic peptides and an anti-CCR5 antibody (mAb CCR5) wherein one to eight antifusogenic peptides are each conjugated to one terminus of the heavy and/or light chains of said anti-CCR5 antibody via a peptide bond. In one embodiment the conjugate according to the invention comprises at least two antifusogenic peptides and an anti-CCR5 antibody wherein two to eight antifusogenic peptides are each conjugated to one terminus of the heavy and/or light chains of said anti-CCR5 antibody.

In one embodiment the conjugate according to the invention is characterized i) in comprising two light chain variable domains of SEQ ID NO:2, two chain conjugates of type (2) each comprising a heavy chain variable domain of SEQ ID NO: 1, a linker of SEQ ID NO:40 and an antifusogenic peptide of SEQ ID NO:33, ii) in comprising two light chain variable domains of SEQ ID NO:4, two chain conjugates of type (2) each comprising a heavy chain variable domain of SEQ ID NO:3, a linker of SEQ ID NO:40 and an antifusogenic peptide of SEQ ID NO:33, iii) in comprising two light chain variable domains of SEQ ID NO:6, two chain conjugates of type (2) each comprising a heavy chain variable domain of SEQ ID NO:5, a linker of SEQ ID NO:40 and an antifusogenic peptide of SEQ ID NO:33, or iv) in comprising two light chain variable domains of SEQ ID NO:8, two chain conjugates of type (2) each comprising a heavy chain variable domain of SEQ ID NO:7, a linker of SEQ ID NO:40 and an antifusogenic peptide of SEQ ID NO:33.

The conjugation between the antifusogenic peptide and the anti-CCR5 antibody is performed on the nucleic acid level. Therefore a peptide bond is formed between the antifusogenic peptide and the anti-CCR5 antibody chain with or without an intermediate linker. Thus either the carboxy-terminal amino acid of the antifusogenic peptide is conjugated to the amino-terminal amino acid of an anti-CCR5 antibody chain with or without an intermediate linker, or a carboxy-terminal amino acid of the anti-CCR5 antibody chain is conjugated to the amino-terminal amino acid of the antifusogenic peptide with or without an intermediate linker or both termini of the anti-CCR5 antibody chain are conjugated to an antifusogenic peptide each with or without an intermediate linker. For the recombinant production of the antifusogenic peptide-anti-CCR5 antibody-conjugate according to the invention one or more nucleic acid molecules encoding different polypeptides are required, preferably two to eight nucleic acid molecules are employed. These nucleic acid molecules encode the different anti-CCR5 antibody polypeptide chains of the conjugate and are in the following referred to as structural genes. They can be located on the same expression plasmid (vector) or can alternatively be located on different expression plasmids (vectors). The assembly of the conjugate takes preferably place before secretion of the conjugate and thus within the expressing cells. Therefore the nucleic acid molecules encoding the polypeptide chains of the conjugate are preferably expressed in the same host cell. If after recombinant expression a mixture of conjugates is obtained, the conjugates can be separated and purified by methods known to a person skilled in the art. These methods are well established and widespread used for immunoglobulin purification and are employed either alone or in combination. Such methods are, for example, affinity chromatography using microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and preparative electrophoretic methods (such as gel electrophoresis, capillary electrophoresis) (M. A. Vijayalakshmi, *Appl. Biochem. Biotech*. (1998) 75:93-102). With recombinant engineering methods known to a person skilled in the art the conjugates can be tailor-made on the nucleic acid/gene level. The nucleic acid sequences encoding immuno-globulins are known and can be obtained for example from genomic databases. Likewise the nucleic acid sequences encoding antifusogenic peptides are known or can easily be deduced from their amino acid sequence. The elements required for the construction of an expression plasmid for the expression of the conjugate of the current invention are, for example, an expression cassette for the anti-CCR5 antibody light chain in its natural and/or modified and/or conjugated version, an expression cassette for the anti-CCR5 antibody heavy chain in its natural and/or modified and/or conjugated version (alternatively the anti-CCR5 antibody light chain and the anti-CCR5 antibody heavy chain can be contained in the same expression cassette, e.g. as bicistronic expression element), a selection marker, and an *E. coli* replication as well as selection unit. These expression cassettes comprise a promoter, a DNA segment encoding a secretion signal sequence, the structural gene, and a terminator/polyadenylation signal. The elements are assembled in an operatively linked form either on one plasmid encoding all chains of the conjugate, or on two or more plasmids each encoding one or more chains of the conjugate. For the expression of the encoded polypeptides the plasmid(s) is (are) introduced into a suitable host cell. Proteins are preferably produced in mammalian cells such as CHO cells, NS0 cells, Sp2/0 cells, COS cells, HEK cells, K562 cells, BHK cells, PER.C6® cells, and the like. The regulatory elements of the plasmid have to be selected in a way that they are functional in the selected host cell. For the expression the host cell containing the plasmid encoding one or more chains of the conjugate is cultivated under conditions suitable for the expression of the chains. The expressed conjugate chains are functionally assembled. The fully processed antifusogenic peptide-anti-CCR5 antibody-conjugate is secreted into the medium.

An "expression plasmid" is a nucleic acid encoding a polypeptide to be expressed in a host cell. Typically, an expression plasmid comprises a prokaryotic plasmid propagation unit, e.g. for E. coli, comprising an origin of replication, and a resistance gene, an eukaryotic selection marker, and one or more expression cassettes for the expression of the structural gene(s) of interest comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

One aspect of the current invention is thus a method for the production of a conjugate according to the invention, comprising the following steps
a) cultivating a cell containing one or more expression plasmids each comprising one or more nucleic acid molecules encoding a conjugate according to the invention under conditions suitable for the expression of the conjugate,
b) recovering the conjugate from the cell or the supernatant.

The term "under conditions suitable for the expression of the conjugate" denotes conditions which are used for the cultivation of a cell expressing a polypeptide and which are known to or can easily be determined by a person skilled in the art. It is known to a person skilled in the art that these conditions may vary depending on the type of cell cultivated and type of polypeptide expressed. In general the cell is cultivated at a temperature, e.g. between 20° C. and 40° C., and for a period of time sufficient to allow effective production of the polypeptide conjugate, e.g. for 4 to 28 days.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion. Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skilled in the art.

Actual dosage levels of the active ingredients in the pharmaceutical compositions of the present invention may be varied so as to obtain an amount of the active ingredient, which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention preferably comprises the use of a conjugate according to the invention for the treatment of a patient suffering from immunodeficiency syndromes such as AIDS.

The following examples, sequence listing, figures and deposits are provided to aid the understanding of the present invention, the true scope of which is set forth in the appended claims. It is understood that modifications can be made in the procedures set forth without departing from the spirit of the invention.

ANTI-CCR5 ANTIBODY DEPOSITION

Figure 1:
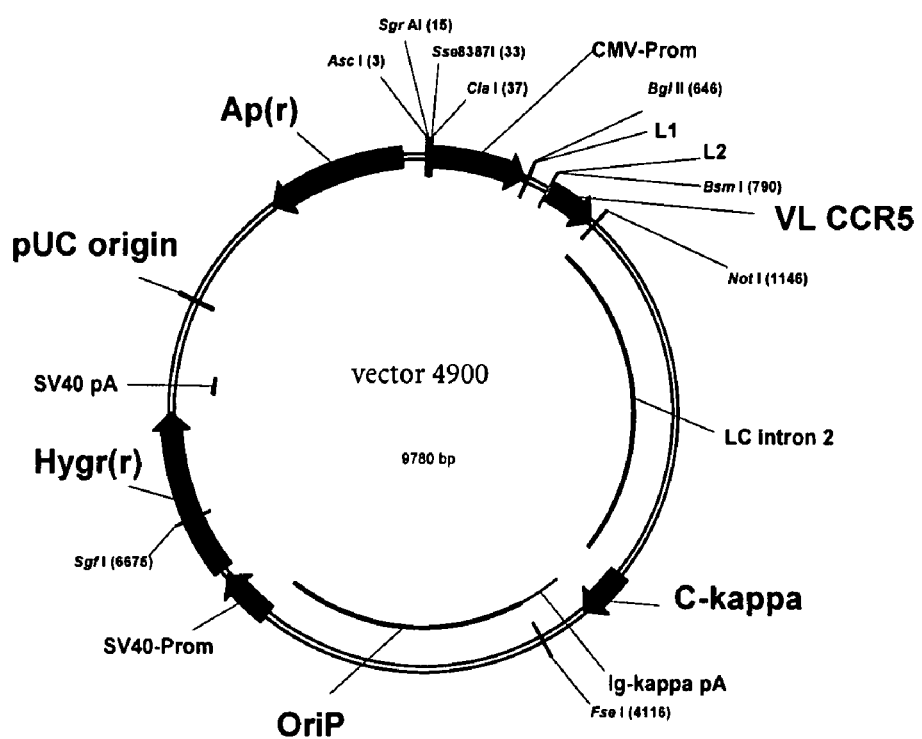
FIG. 1: Plasmid map of mab CCR5 κ-light chain expression vector 4900.

Preferred hybridoma cell lines expressing mAb CCR5 useful in the conjugates according to the invention were deposited with Deutsche Sammlung von Mikroorganismen und Zellkulturen GmbH (DSMZ), Germany.

| Cell line | Deposition No. | Date of Deposit |
|---|---|---|
| m<CCR5>Pz01.F3 | DSM ACC 2681 | 18 Aug. 2004 |
| m<CCR5>Pz02.1C11 | DSM ACC 2682 | 18 Aug. 2004 |
| m<CCR5>Pz03.1C5 | DSM ACC 2683 | 18 Aug. 2004 |
| m<CCR5>Pz04.1F6 | DSM ACC 2684 | 18 Aug. 2004 |

Antibody Nomenclature

| | | |
|---|---|---|
| <CCR5>Pz01.F3: | Antibody A | SEQ ID NO: 1, 2 |
| <CCR5>Pz02.1C11: | Antibody B | SEQ ID NO: 3, 4 |
| <CCR5>Pz03.1C5: | Antibody C | SEQ ID NO: 5, 6 |
| <CCR5>F3.1H12.2E5: | Antibody D | SEQ ID NO: 7, 8 |
| <CCR5>Pz04.1F6: | Antibody E | |

CCR 5 Antibody Sequences, Sequences of Antifusogenic Peptides and Sequences of Peptidic Linkers

| | |
|---|---|
| SEQ ID NO: 1 | <CCR5>Pz01.F3 heavy chain, variable domain |
| SEQ ID NO: 2 | <CCR5>Pz01.F3 light chain, variable domain |
| SEQ ID NO: 3 | <CCR5>Pz02.1C11 heavy chain, variable domain |
| SEQ ID NO: 4 | <CCR5>Pz02.1C11 light chain, variable domain |
| SEQ ID NO: 5 | <CCR5>Pz03.1C5 heavy chain, variable domain |
| SEQ ID NO: 6 | <CCR5>Pz03.1C5 light chain, variable domain |
| SEQ ID NO: 7 | <CCR5>F3.1H12.2E5 heavy chain, variable domain |

-continued

| SEQ ID NO: 8 | <CCR5>F3.1H12.2E5 light chain, variable domain |
| --- | --- |
| SEQ ID NO: 9 | Heavy chain CDR1 |
| SEQ ID NO: 10 | Heavy chain CDR1 |
| SEQ ID NO: 11 | Heavy chain CDR1 |
| SEQ ID NO: 12 | Heavy chain CDR1 |
| SEQ ID NO: 13 | Heavy chain CDR2 |
| SEQ ID NO: 14 | Heavy chain CDR2 |
| SEQ ID NO: 15 | Heavy chain CDR2 |
| SEQ ID NO: 16 | Heavy chain CDR3 |
| SEQ ID NO: 17 | Heavy chain CDR3 |
| SEQ ID NO: 18 | Light chain CDR1 |
| SEQ ID NO: 19 | Light chain CDR1 |
| SEQ ID NO: 20 | Light chain CDR1 |
| SEQ ID NO: 21 | Light chain CDR2 |
| SEQ ID NO: 22 | Light chain CDR2 |
| SEQ ID NO: 23 | Light chain CDR2 |
| SEQ ID NO: 24 | Light chain CDR3 |
| SEQ ID NO: 25 | Light chain CDR3 |
| SEQ ID NO: 26 | γ1 heavy chain constant region |
| SEQ ID NO: 27 | γ4 heavy chain constant region |
| SEQ ID NO: 28 | κ light chain constant domain |
| SEQ ID NO: 29 | C34 |
| SEQ ID NO: 30 | T20 |
| SEQ ID NO: 31 | T1249 |
| SEQ ID NO: 32 | T651 |
| SEQ ID NO: 33 | T2635 |
| SEQ ID NO: 34 | N36 |
| SEQ ID NO: 35 | DP107 |
| SEQ ID NO: 36-62 | linker peptides |
| SEQ ID NO: 63 | Amino acid sequence of mature mAb CCR5 κ-light chain |
| SEQ ID NO: 64 | Amino acid sequence of mature mAb CCR5 γ1-heavy chain |
| SEQ ID NO: 65 | Amino acid sequence of mature mAb CCR5 conjugate heavy chain |
| SEQ ID NO: 66 | HIV-1 gp41 |

TABLE 2

Linker

| No. | Linker peptides | SEQ ID NO: |
| --- | --- | --- |
| 1 | LSLSPGK | 36 |
| 2 | LSPNRGEC | 37 |
| 3 | $[GQ_4]_3$ | 38 |
| 4 | $[GQ_4]_3G$ | 39 |
| 5 | $[GQ_4]_3GNN$ | 40 |
| 6 | $GGG[SG_4]_2SGG$ | 41 |
| 7 | $GGG[SG_4]_2SGN$ | 42 |
| 8 | $[SG_4]_3$ | 43 |
| 9 | $[SG_4]_3G$ | 44 |
| 10 | $G[SG_4]_3T$ | 45 |
| 11 | $[SG_4]_3GG$ | 46 |
| 12 | $[SG_4]_3GGT$ | 47 |
| 13 | $[SG_4]_3GGN$ | 48 |
| 14 | $[SG_4]_3GAS$ | 49 |
| 15 | $[SG_4]_5$ | 50 |
| 16 | $[SG_4]_5G$ | 51 |
| 17 | $[SG_4]_5GG$ | 52 |
| 18 | $[SG_4]_5GAS$ | 53 |
| 19 | $G(S)_{15}G$ | 54 |
| 20 | $G(S)_{15}GAS$ | 55 |
| 21 | G | — |
| 22 | N | — |
| 23 | GST | — |
| 24 | $[(G)_4S]_3GAS$ | 56 |
| 25 | $[(G)_4S]_3G$ | 57 |
| 26 | $[(G)_4S]_5G$ | 58 |
| 27 | $[(G)_4S]_3GG$ | 59 |
| 28 | $[(G)_4S]_5GG$ | 60 |
| 29 | LSLSGG | 61 |
| 30 | LSLSPGG | 62 |

EXAMPLES

Materials & Methods

General information regarding the nucleotide sequences of human immunoglobulins light and heavy chains is given in: E. A. Kabat et al., Sequences of Proteins of Immunological Interest, 5th ed., Public Health Service, National Institutes of Health, Bethesda, Md. (1991). Amino acids of antibody chains are numbered according to EU numbering (G. M. Edelman et al., *Proc. Natl. Acad. Sci. USA* (1969) 63: 78-85; E. A. Kabat et al., supra).

Recombinant DNA Techniques

Standard methods were used to manipulate DNA as described in J. Sambrook et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The 100-600 bp long gene segments, which are flanked by singular restriction endonuclease cleavage sites, were assembled by annealing and ligation of oligonucleotides including PCR amplification and subsequently cloned into the pCR2.1-TOPO-TA cloning vector (Invitrogen Corp., USA) via A-overhangs. The DNA sequence of the subcloned gene fragments were confirmed by DNA sequencing.

Protein Determination

The protein concentration of the conjugate was determined by determining the optical density (OD) at 280 nm, using the molar extinction coefficient calculated on the basis of the amino acid sequence.

Example 1

Synthesizing the Expression Plasmids

The gene segments encoding an anti-CCR5 antibody light chain variable domain ($V_L$) and the human kappa-light chain constant domain ($C_L$) were joined as were gene segments for the anti-CCR5 antibody heavy chain variable domain ($V_H$) and the human γ1-heavy chain constant domains ($C_H1$-Hinge-$C_H2$-$C_H3$).

In the case of mAb CCR5 of SEQ ID NO:63/64 the heavy and light chain variable domains are derived from a mouse antibody and the heavy and light chain constant domains are derived from a human antibody (C-kappa and IgG1).

Subsequently, the gene segment encoding a complete anti-CCR5 antibody light chain was joined at the N- and/or C-terminus with a nucleic acid encoding an antifusogenic peptide including a connecting linker sequence and/or the gene segment encoding a complete anti-CCR5 antibody heavy chain was joined at the N- and/or C-terminus with a nucleic acid encoding an antifusogenic peptide including a connecting linker sequence.

a) Vector 4900

Vector 4900 is an expression plasmid for transient expression of a mAb CCR5 light chain (genomically organized expression cassette; exon-intron organization) in HEK293 cells.

Beside the mAb CCR5 κ-light chain expression cassette this vector contains:
a hygromycine resistance gene as a selectable marker,
an origin of replication, oriP, of Epstein-Barr virus (EBV),
an origin of replication from the vector pUC18 which allows replication of this plasmid in *E. coli*, and a β-lactamase gene which confers ampicillin resistance in *E. coli*.

The transcription unit of the mAb CCR5 κ-light chain gene is composed of the following elements:
- the immediate early enhancer and promoter from the human cytomegalovirus,
- a synthetic 5'-untranslated region,
- a murine immunoglobulin heavy chain signal sequence including a signal sequence intron (signal sequence 1, intron, signal sequence 2 [L1-intron-L2]),
- the murine anti-CCR5 antibody mature variable κ-light chain encoding segment arranged with a unique BsmI restriction site at the 5'-end (L2 signal sequence) and a splice donor site and a unique NotI restriction site at the 3'-end,
- a human/mouse κ-light chain hybrid intron 2,
- the human κ-light gene constant domain,
- the human immunoglobulin K-polyadenylation ("poly A") signal sequence, and
- the unique restriction sites AscI and FseI at the 5'- and 3'-end, respectively.

The plasmid map of the mAb CCR5 κ-light chain expression vector 4900 is shown in FIG. 1. The amino acid sequence of the mature (without signal sequence) mAb CCR5 κ-light chain is shown in SEQ ID NO:63.

b) Vector 4991

Vector 4991 is an expression plasmid for transient expression of a mAb CCR5 γ1-heavy chain (genomically organized expression cassette; exon-intron organization) in HEK293 cells.

Beside the mAb CCR5 γ1-heavy chain expression cassette this vector contains:
- a hygromycin resistance gene as a selectable marker,
- an origin of replication, oriP, of Epstein-Barr virus (EBV),
- an origin of replication from the vector pUC18 which allows replication of this plasmid in *E. coli*, and
- a beta-lactamase gene which confers ampicillin resistance in *E. coli*.

The transcription unit of the mAb CCR5 γ1-heavy chain is composed of the following elements:
- the immediate early enhancer and promoter from the human cytomegalovirus,
- a synthetic 5'-untranslated region,
- a murine immunoglobulin heavy chain signal sequence including a signal sequence intron (signal sequence 1, intron, signal sequence 2 [L1-intron-L2]),
- the murine anti-CCR5 antibody mature variable heavy chain encoding segment arranged with a unique BsmI restriction site at the 5'-end (L2 signal sequence) and a splice donor site and a unique NotI restriction site at the 3'-end,
- a human/mouse heavy chain hybrid intron 2 including the mouse heavy chain enhancer element (part $JH_3$, $JH_4$) (Neuberger, M. S., EMBO J. 2 (1983) 1373-1378),
- the genomic human γ1-heavy gene constant domains,
- the human γ1-immunoglobulin polyadenylation ("poly A") signal sequence, and
- the unique restriction sites AscI and SgrAI at the 5'- and 3'-end, respectively.

Figure 2:
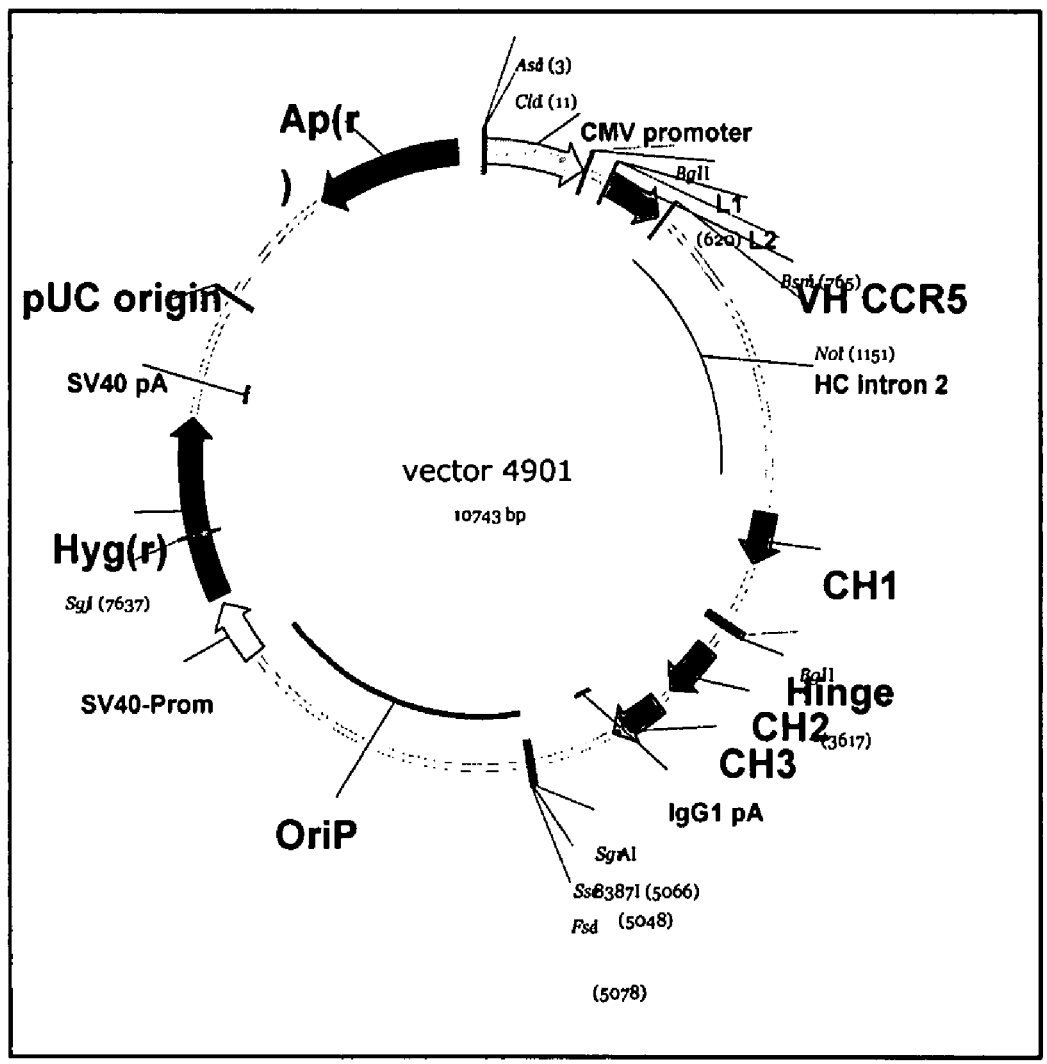
FIG. 2: Plasmid map of mAb CCR5 γ1-heavy chain expression vector 4901.

The plasmid map of the mAb CCR5 γ1-heavy chain expression vector 4901 is shown in FIG. 2. The amino acid sequence of the mature (without signal sequence) mAb CCR5 γ1-heavy chain is shown in SEQ ID NO:64.

c) Vector 4995

Vector 4995 is an expression plasmid for transient expression of a chimeric peptide-anti-CCR5 antibody γ1-heavy chain conjugate (genomically organized expression cassette; exon-intron organization) in HEK293 cells.

The vector 4995 is derived from plasmid 4991 in that way that the mAb CCR5 γ1-heavy chain is joint at the C-terminus with a nucleic acid encoding the antifusogenic peptide T-2635 (SEQ ID NO:33) and the peptidic linker sequence $[GQ_4]_3GNN$ (SEQ ID NO:40).

Beside the chimeric peptide anti-CCR5 antibody γ1-heavy chain conjugate expression cassette this vector contains:
- a hygromycin resistance gene as a selectable marker,
- an origin of replication, oriP, of Epstein-Barr virus (EBV),
- an origin of replication from the vector pUC18 which allows replication of this plasmid in *E. coli*, and
- a beta(β)-lactamase gene which confers ampicillin resistance in *E. coli*.

The transcription unit of the chimeric peptide-anti-CCR5 antibody γ1-heavy chain conjugate is composed of the following elements:
- the immediate early enhancer and promoter from the human cytomegalovirus,
- a synthetic 5'-untranslated region,
- a murine immunoglobulin heavy chain signal sequence including a signal sequence intron (signal sequence 1, intron, signal sequence 2 [L1-intron-L2]),
- the murine anti-CCR5 antibody mature variable heavy chain encoding segment arranged with a unique BsmI restriction site at the 5'-end (L2 signal sequence) and a splice donor site and a unique NotI restriction site at the 3'-end,
- a human/mouse heavy chain hybrid intron 2 including the mouse heavy chain enhancer element (part $JH_3$, $JH_4$) (Neuberger, M. S., EMBO J. 2 (1983) 1373-1378),
- the genomic human γ1-heavy gene constant domains,
- the antifusogenic peptide T-2635,
- the peptidic linker sequence $[GQ_4]_3GNN$,
- the human γ1-immunoglobulin polyadenylation ("poly A") signal sequence, and
- the unique restriction sites AscI and SgrAI at the 5'- and 3'-end, respectively.

Figure 3:
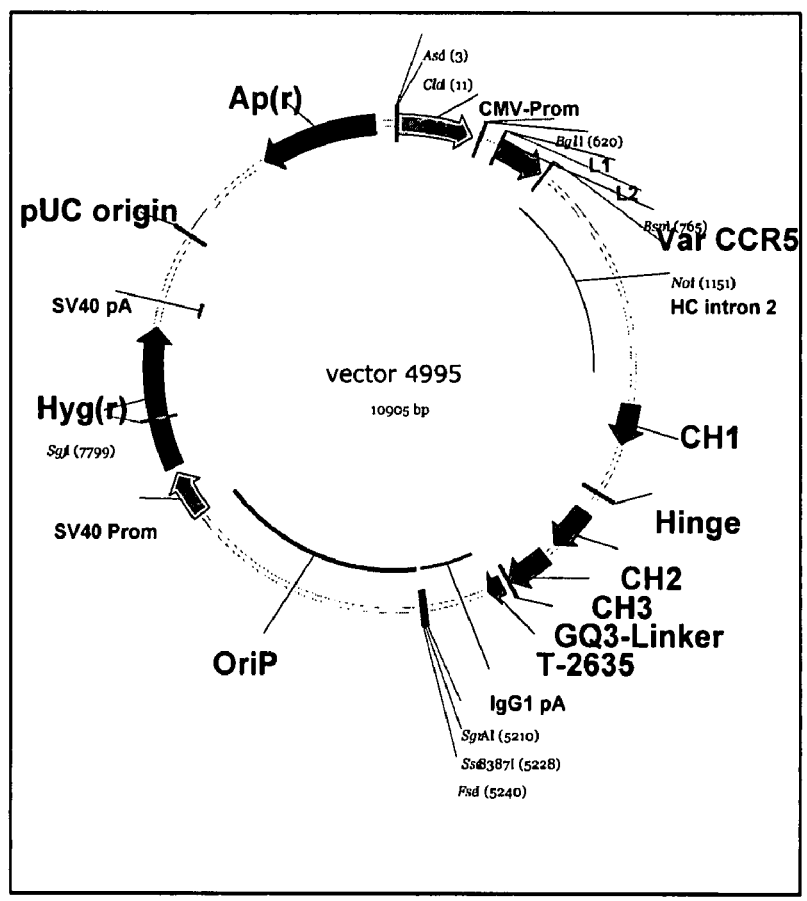
FIG. 3: Plasmid map of mAb CCR5 γ1-heavy chain conjugate expression vector 4995.

The plasmid map of the mAb CCR5 γ1-heavy chain conjugate expression vector 4995 is shown in FIG. 3. The amino acid sequence of the mature (without signal sequence) conjugate heavy chain is shown in SEQ ID NO:65.

Example 2

Making of the Final Expression Plasmids

The fusion genes (heavy and/or light chain antibody fusion genes) comprising a mAb CCR5 gene segment, an optional linker gene segment and an antifusogenic peptide gene segment have been assembled with known recombinant methods and techniques by connection of the according nucleic acid segments. The nucleic acid sequences encoding the peptidic linkers and antifusogenic polypeptides were each synthesized by chemical synthesis and then ligated into an *E. coli* plasmid for amplification. The subcloned nucleic acid sequences were verified by DNA sequencing.

Example 3

Transient Expression of Immunoglobulins and Immunoglobulin Variants in HEK293 EBNA Cells Recombinant anti-CCR5 antibodies and anti-CCR5 antibody-variants were generated by transient transfection of adherent growing HEK293-EBNA cells (human embryonic kidney cell line 293 expressing Epstein-Barr-Virus nuclear antigen; American type culture collection deposit number ATCC # CRL-10852) cultivated in DMEM (Dulbecco's modified Eagle's medium, Gibco) supplemented with 10% ultra-low IgG FCS (fetal calf serum, Gibco), 2 mM Glutamine (Gibco), 1% volume by volume (v/v) nonessential amino acids (Gibco) and 250 µg/ml G418 (Roche Molecular Biochemicals). For transfection FuGENE™ 6 Transfection Reagent (Roche Molecular Biochemicals) was used in a ratio of reagent (µl) to DNA (µg) ranging from 3:1 to 6:1. Light and heavy chains including antifusogenic peptide-anti-CCR5 antibody conjugate light and heavy chains were expressed from two different plasmids using a molar ratio of light chain to heavy chain encoding plasmid ranging from 1:2 to 2:1, respectively. Antifusogenic peptide-anti-CCR5 antibody conjugates containing cell culture supernatants were harvested at day 4 to 11 after transfection. General information regarding the recombinant expression of human immunoglobulins in e.g. HEK293 cells is given in P. Meissner et al., *Biotechnol. Bioeng.* (2001) 75:197-203.

Example 4

Expression Analysis using SDS PAGE, Western Blotting Transfer and Detection with Immunoglobulin Specific Antibody Conjugates The expressed and secreted antifusogenic peptide-anti-CCR5 antibody conjugates were processed by sodium dodecyl sulfate (SDS) polyacrylamide gel electrophoresis (SDS-PAGE), and the separated anti-CCR5-antibody and antifusogenic peptide-anti-CCR5-antibody-conjugate chains were transferred to a membrane from the gel and subsequently detected by an immunological method.
SDS-PAGE LDS sample buffer, fourfold concentrate (4×): 4 g glycerol, 0.682 g TRIS-Base, 0.666 g TRIS-hydrochloride, 0.8 g LDS (lithium dodecyl sulfate), 0.006 g EDTA (ethylene diamin tetra acid), 0.75 ml of a 1% by weight (w/w) solution of Serva Blue G250 in water, 0.75 ml of a 1% by weight (w/w) solution of phenol red, add water to make a total volume of 10 ml.

The culture broth containing the secreted antifusogenic peptide-anti-CCR5 antibody conjugate was centrifuged to remove cells and cell debris. An aliquot of the clarified supernatant was admixed with ¼ volumes (v/v) of 4xLDS sample buffer and 1/10 volume (v/v) of 0.5 M 1,4-dithiotreitol (DTT). Then the samples were incubated for 10 min. at 70° C. and protein separated by SDS-PAGE. The NuPAGE® Pre-Cast gel system (Invitrogen) was used according to the manufacturer's instruction. In particular, 10% NuPAGE® Novex® Bis-TRIS Pre-Cast gels (pH 6.4) and a NuPAGE® MOPS running buffer was used.
Western Blot Transfer buffer: 39 mM glycine, 48 mM TRIS-hydrochloride, 0.04% by weight (w/w) SDS, and 20% by volume methanol (v/v).

After SDS-PAGE the separated antifusogenic peptide-anti-CCR5 antibody conjugate chains were transferred electrophoretically to a nitrocellulose filter membrane (pore size: 0.45 µm) according to the "Semidry-Blotting-Method" of Burnette (W. N. Burnette, *Anal. Biochem.* (1981) 112:195-203).
Immunological Detection TBS-buffer: 50 mM TRIS-hydrochloride, 150 mM NaCl, adjusted to pH 7.5 Blocking solution: 1% (w/v) Western Blocking Reagent (Roche Molecular Biochemicals) in TBS-buffer TBST-Buffer: 1×TBS-buffer with 0.05% by volume (v/v) Tween-20 For immunological detection the western blotting membranes were incubated with shaking at room temperature two times for 5 minutes in TBS-buffer and once for 90 minutes in blocking solution.
Detection of the Peptide Immunoglobulin Conjugate Chains Heavy chain: For detection of the heavy chain of the antifusogenic peptide-anti-CCR5 antibody conjugate a purified rabbit anti-human IgG antibody conjugated to a peroxidase was used (DAKO, Code No. P 0214).

Light chain: The light chain of the antifusogenic peptide-anti-CCR5 antibody conjugate was detected with a purified peroxidase conjugated rabbit anti-human kappa light chain antibody (DAKO, Code No. P 0129).

For visualization of the antibody light and heavy chains washed and blocked Western blot membranes were first incubated in case of a heavy chain with a purified rabbit anti-human IgG antibody conjugated to a peroxidase or in case of a light chain with a purified peroxidase conjugated rabbit anti-human kappa light chain antibody in a 1:10,000 dilution in 10 ml blocking solution at 4° C. with shaking over night. After washing the membranes three times with TBTS-buffer and once with TBS buffer for 10 min. at room temperature, the Western-blot membranes were developed with a Luminol/peroxid-solution generating chemiluminescence (Lumi-Light$^{PLUS}$ Western Blotting Substrate, Roche Molecular Biochemicals). Therefore the membranes were incubated in 10 ml Luminol/peroxid-solution for 10 seconds to 5 minutes and the emitted light was detected afterwards with a LUMI-Imager F1 Analysator (Roche Molecular Biochemicals) and/or was recorded with an x-ray-film. The intensity of the spots was quantified with the LumiAnalyst Software (Version 3.1).
Multiple-Staining of Immunoblots The secondary peroxidase-labeled antibody conjugate used for the detection can be removed from the stained blot by incubating the membrane for one hour at 70° C. in 1 M TRIS-hydrochloride-buffer (pH 6.7) containing 100 mM beta-mercaptoethanol and 20% (w/v) SDS. After this treatment the blot can be stained with a different secondary antibody a second time. Prior to the second detection the blot is washed three times at room temperature with shaking in TBS-buffer for 10 minutes each.

Example 5

Affinity Purification, Dialysis and Concentration of Peptide Immunoglobulin Conjugates The expressed and secreted antifusogenic peptide-anti-CCR5 antibody conjugates were purified by affinity chromatography using Protein A-Sepharose™ CL-4B (GE Healthcare former Amersham Bioscience, Sweden) according to known methods. Briefly, after centrifugation (10,000 g for 10 minutes) and filtration through a 0.45 µm filter the peptide immunoglobulin conjugate containing clarified culture supernatants were applied on a Protein A-Sepharose™ CL-4B column equilibrated with PBS buffer (10 mM Na$_2$HPO$_4$, 1 mM KH$_2$PO$_4$, 137 mM NaCl and 2.7 mM KCl, pH 7.4). Unbound proteins were washed out with PBS equilibration buffer and 0.1 M citrate buffer, pH 5.5. The antifusogenic peptide-anti-CCR5 antibody conjugates were eluted with 0.1 M citrate buffer, pH 3.0, and the conjugate containing fractions were neutralized with 1 M TRIS-Base. Then, the antifusogenic peptide-anti-CCR5 antibody conjugates were extensively dialyzed against PBS buffer at 4° C., concentrated with a Ultrafree®-CL Centrifugal Filter Unit equipped with a Biomax-SK membrane (Millipore Corp., USA) and stored in an ice-water bath at 0° C. The integrity of the conjugates was analyzed by SDS-PAGE in the presence and absence of a reducing agent and staining with Coomassie brilliant blue as described in example 4. Aggregation of antifusogenic peptide-anti-CCR5 antibody conjugates was analyzed by analytical size exclusion chromatography.

Example 6

Deglycosylation of Peptide Immunoglobulin Conjugates

N-linked carbohydrates of anti-CCR5 antibodies and antifusogenic peptide-anti-CCR5 antibody conjugates were cleaved off by enzymatic treatment with Peptide-N-Glycosidase F (PNGaseF, Roche Molecular Biochemicals, Mannheim, Germany or Prozyme, San Leandro, Calif.). Therefore, the anti-CCR5 antibodies and antifusogenic peptide-anti-CCR5 antibody conjugates were incubated at 37° C. for 12-24 h using 50 mU PNGaseF per mg N-glycosylated protein in PBS buffer at a protein concentration of about 2 mg/ml. Thereafter the Peptide-N-Glycosidase F was separated by preparative gel filtration according to known methods. Briefly, PNGaseF treated anti-CCR5-antibodies and antifusogenic peptide-anti-CCR5 antibody conjugates were applied on a Superose™ 12 10/300 GL column (GE Healthcare former Amersham Bioscience, Sweden) equilibrated with PBS buffer (10 mM $Na_2HPO_4$, 1 mM $KH_2PO_4$, 137 mM NaCl and 2.7 mM KCl, pH 7.4) and then eluted with equilibration buffer at a flow rate of 0.5-1.0 ml/min using the Äkta explorer chromatography system from Amersham Bioscience (GE Healthcare former Amersham Bioscience, Sweden).

Example 7

Single-Cycle Antiviral Activity Assay

For the production of pseudotyped NL-Bal viruses, plasmid pNL4-3Δenv (HIV pNL4-3 genomic construct with a deletion within the env gene) and pcDNA3.1/NL-BAL env [pcDNA3.1 plasmid containing NL-Bal env gene (obtained from NIBSC Centralized Facility for AIDS Reagents)] were co-transfected into the HEK 293FT cell line (Invitrogen), cultured in Dulbecco's modified minimum medium (DMEM) containing 10% fetal calf serum (FCS), 100 U/mL Penicillin, 100 μg/mL Streptomycin, 2 mM L-glutamine and 0.5 mg/mL geniticin (all media from Invitrogen/Gibco). The supernatants containing pseudotyped viruses were harvested two days following transfection, and cellular debris was removed by filtration through a 0.45 μm pore size PES (polyethersulfone) filter (Nalgene) and stored at −80° C. in aliquots. For normalization in assay performance, virus stock aliquots were used to infect JC53-BL (US NIH Aids Reagent Program) cells yielding approximately $1.5 \times 10^5$ RLU (relative light units) per well. Test antifusogenic peptide-anti-CCR5 antibody conjugates, reference antibodies and reference antifusogenic peptides (T-20, T-1249, T-651 and T-2635) were serially diluted in 96-well plates. The assay was carried out in quadruplicates. Each plate contained cell control and virus control wells. The equivalent of $1.5 \times 10^5$ RLU of virus stocks were added to each well, then $2.5 \times 10^4$ JC53-BL cells were added to each well, with a final assay volume of 200 μl per well. After 3 day incubation at 37° C., 90% Relative Humidity, and 5% $CO_2$, media were aspirated and 50 μl of Steady-Glo® Luciferase Assay System (Promega) was added to each well. The assay plates were read on a Luminometer (Luminoskan, Thermo Electron Corporation) after 10 minutes of incubation at room temperature. Percent inhibition of luciferase activity was calculated for each dose point after subtracting the background, and $IC_{50}$ and $IC_{90}$-values were determined by using XLfit curve fitting software for Excel (version 3.0.5 Build12; Microsoft). Results are shown in Table 3.

TABLE 3

Antiviral activity of antifusogenic polypeptides, antibodies and antifusogenic peptide-anti-CCR5 antibody conjugates

| Compound | Antiviral activity | |
|---|---|---|
| | $IC_{50}$ (ng/mL) | $IC_{90}$ (ng/mL) |
| Reference antibody 1 (inert) | inactive | inactive |
| Reference antibody 2 (inert) | inactive | inactive |
| T-20 | 206 | 3955 |
| T-1249 | 11 | 90 |
| T-651 | 11 | 139 |
| T-2635 | 14 | 161 |
| mAb CCR5 (4901/4900) | 114 | 2387 |
| Chimeric peptide mAb CCR5 conjugate (4995/4900) | 7 | 45 |

Example 8

Cell-Cell Fusion Assay

At day 1, gp160-expressing HeLa cells ($2 \times 10^4$ cells/50 μl/well) are seeded in a white 96 microtiter plate in DMEM medium supplemented with 10% FCS and 2 μg/ml doxycycline. At day 2, 100 μl of supernatant sample or antibody control per well is added in a clear 96 microtiter plate. Then 100 μl containing $8 \times 10^4$ CEM-NKr-Luc suspension cells in medium are added and incubated 30 min. at 37° C. The HeLa cell culture medium is aspirated from the 96 well plate, 100 μl from the 200 μl antibody/CEM-NKr-Luc mixture is added and incubated overnight at 37° C. At day 3, 100 μl/well Bright-Glo™ Luciferase assay substrate (1,4-dithiothreitol and sodium dithionite; Promega Corp., USA) is added and luminescence is measured after a minimum of 15 min. incubation at RT.

Materials:

HeLa-R5-16 cells (cell line to express HIV gp160 upon doxycycline induction) are cultured in DMEM medium containing nutrients and 10% FCS with 400 μg/ml G418 and 200 μg/ml Hygromycin B. CEM.NKR-CCR5-Luc (Catalog Number: 5198, a T-cell line available from NIH AIDS Research & Reference Reagent Program McKesson BioServices Corporation Germantown, Md. 20874, USA). Cell Type: CEM.NKR-CCR5 (Cat. #4376) is transfected (electroporation) to express the luciferase gene under the transcriptional control of the HIV-2 LTR and propagated in RPMI 1640 containing 10% fetal bovine serum, 4 mM glutamine, penicillin/streptomycin (100 U/mL Penicillin, 100 μg/mL Streptomycin), and 0.8 mg/ml geniticin sulfate (G418). Growth Characteristics: Round lymphoid cells, morphology not very variable. Cells grow in suspension as single cells, which can form small clumps. Split 1:10 twice weekly. Special Characteristics: Express luciferase activity after transactivation of the HIV-2 LTR. Suitable for infection with primary HIV isolates, for neutralization and drug-sensitivity assays (C. Spenlehauer et al., *Virology* (2001) 280:292-300; A. Trkola et al., *J. Virol*. (1999) 73:8966-74). The cell line was obtained through the NIH AIDS Research and Reference Reagent Program, NIAID, NIH from Drs. John Moore and Catherine Spenlehauer. Bright-Glo™ Luciferase assay buffer (Promega Corp. USA, Part No E2264B), Bright-Glo™, Luciferase assay substrate (Promega Corp. USA, part No EE26B).

Example 9

Antiviral Activity Assay in Peripheral Blood Mononuclear Cells (PBMC)

Human PBMC are isolated from buffy-coats (obtained from the Stanford Blood Center) by a Ficoll-Paque (Amersham, Piscataway, N.J., USA) density gradient centrifugation according to manufacturer's protocol. Briefly, blood is transferred from the buffy coats in 50 ml conical tubes and diluted with sterile Dulbecco's phosphate buffered saline (Invitrogen/Gibco) to a final volume of 50 ml. Twenty-five ml of the diluted blood are transferred to two 50 ml conical tubes, carefully underlayered with 12.5 ml of Ficoll-Paque Plus (Amersham Biosciences) and centrifuged at room temperature for 20 min. at 450×g without braking. The white cell layer is carefully transferred to a new 50 ml conical tube and washed twice with PBS. To remove remaining red blood cells, cells are incubated for 5 min. at room temperature with ACK lysis buffer (Biosource) and washed one more time with PBS. PBMC are counted and incubated at a concentration of 2-4× $10^6$ cells/ml in RPMI1640 containing 10% FCS (Invitrogen/Gibco), 1% penicillin/streptomycin, 2 mM L-glutamine, 1 mM sodium-pyruvate, and 2 µg/ml Phytohemagglutinin (Invitrogen) for 24 h at 37° C. Cells are incubated with 5 Units/ml human IL-2 (Roche Molecular Biochemicals) for a minimum of 48 h prior to the assay. In a 96 well round bottom plate, $1\times10^5$ PBMC are infected with the HIV-1 JR-CSF virus (Y. Koyanagi et al., *Science* (1987) 236:819-22) in the presence of serially diluted test peptide-immunoglobulin-conjugates, reference immunoglobulins and reference peptides (T-20, T-1249, T-651 and T-2635). The amount of virus used is equivalent to 1.2 ng HIV-1 p24 antigen/well. Infections are set up in quadruplicates. Plates are incubated for 6 days at 37° C. Virus production is measured at the end of infection by using p24 ELISA (HIV-1 p24 ELISA #NEK050B, Perkin Elmer/NEN) using the sigmoid dose-response model with one binding site in Microsoft Excel Fit (version 3.0.5 Build 12; equation 205; Microsoft).

The invention claimed is:

1. A conjugate comprising an anti-CCR5 antibody (mAb CCR5) comprising two heavy chains and two light chains, having termini comprising an N-terminus and a C-terminus, wherein two or four of said N-terminus or said C-terminus are conjugated with an antifusogenic peptide; wherein said anti-CCR5 antibody comprises a variable heavy chain domain and a variable light chain domain, wherein said variable heavy chain domain consists of an immunoglobulin framework and a CDR3 region selected from the group consisting of heavy chain CDR3 sequences SEQ ID NOS:16 and 17; a CDR2 region selected from the group consisting of heavy chain CDR2 sequences SEQ ID NOS:13, 14, and 15; and a CDR1 region selected from the group consisting of heavy chain CDR1 sequences SEQ ID NOS:9, 10, 11, and 12; and wherein said variable light chain domain consists of an immunoglobulin framework and a CDR1 region selected from SEQ ID NOS:18, 19, and 20; a CDR2 region selected from SEQ ID NOS:21, 22, and 23; and a CDR3 region selected from SEQ ID NOS:24 and 25.

2. The conjugate of claim 1, wherein said antifusogenic peptide has a sequence selected from the group consisting of SEQ ID NOS:29 to 35.

3. A conjugate comprising an anti-CCR5 antibody (mAb CCR5) comprising two heavy chains and two light chains, having termini comprising an N-terminus and a C-terminus, wherein two or four of said N-terminus or said C-terminus are conjugated with an antifusogenic peptide; wherein said anti-CCR5 antibody is of IgG4 subclass, or is of IgG1 or IgG2 subclass with a mutation in amino acid 5228, L234, L235, and/or D265, and/or contains the PVA236 mutation.

4. A conjugate according to claim 3, wherein said anti-CCR5 antibody of IgG4 subclass has the mutation S228P and said anti-CCR5 antibody of IgG1 subclass has the mutations L234A and L235A.

5. A pharmaceutical composition, comprising an effective amount of a conjugate of claim 1, together with a pharmaceutically acceptable excipient or carrier.

* * * * *

SEQUENCE LISTING

```
<160> NUMBER OF SEQ ID NOS: 66

<210> SEQ ID NO 1
<211> LENGTH: 119
<212> TYPE: PRT
<213> ORGANISM: mouse

<400> SEQUENCE: 1

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Ser Ile Ser Thr Gly Asp Asn Thr Tyr Tyr Thr Asp Ser Val Arg
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Phe Cys Thr
                85                  90                  95

Arg Gly Arg Gly Asp Arg Gly Asp Leu Phe Gly Tyr Trp Gly Gln Gly
            100                 105                 110

Thr Leu Val Thr Val Ser Ser
        115

<210> SEQ ID NO 2
<211> LENGTH: 114
<212> TYPE: PRT
<213> ORGANISM: mouse

<400> SEQUENCE: 2

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Arg
            20                  25                  30

Gly Asn Gln Met Asn Tyr Leu Ala Trp Tyr Gln Gln Lys Pro Gly Gln
        35                  40                  45
```

```
Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Glu Phe Thr Leu Thr
65                  70                  75                  80

Ile Ser Ser Val Lys Ala Glu Asp Leu Thr Val Tyr Tyr Cys Gln Gln
                85                  90                  95

Tyr Tyr Thr Tyr Pro Arg Thr Phe Gly Gly Gly Thr Lys Leu Glu Ile
            100                 105                 110

Lys Arg

<210> SEQ ID NO 3
<211> LENGTH: 117
<212> TYPE: PRT
<213> ORGANISM: mouse

<400> SEQUENCE: 3

Gln Val Gln Leu Lys Gln Ser Gly Pro Gly Leu Val Arg Pro Ser Gln
1               5                   10                  15

Ser Leu Ser Ile Thr Cys Thr Val Ser Gly Phe Pro Leu Gly Val Phe
                20                  25                  30

Gly Val His Trp Val Arg Gln Ser Pro Gly Lys Gly Leu Glu Trp Leu
            35                  40                  45

Gly Val Ile Trp Lys Gly Gly Asn Thr Asp Tyr Asn Ala Ala Phe Met
        50                  55                  60

Ser Arg Leu Arg Ile Ser Lys Asp Asn Ser Lys Ser Gln Val Phe Phe
65                  70                  75                  80

Arg Met Asn Ser Leu Gln Thr Asp Asp Thr Ala Ile Tyr Tyr Cys Ala
                85                  90                  95

Lys Val Asn Leu Ala Asp Ala Met Asp Tyr Trp Gly Gln Gly Thr Ser
            100                 105                 110

Val Ile Val Ser Ser
            115

<210> SEQ ID NO 4
<211> LENGTH: 108
<212> TYPE: PRT
<213> ORGANISM: mouse

<400> SEQUENCE: 4

Asp Ile Gln Met Thr Gln Ser Pro Ala Ser Leu Ser Ala Ser Val Gly
1               5                   10                  15

Glu Thr Val Thr Ile Thr Cys Arg Ser Ser Gly Asn Ile His Gly Tyr
                20                  25                  30

Leu Ala Trp Phe Gln Gln Lys Gln Gly Lys Ser Pro Gln Leu Leu Val
            35                  40                  45

Tyr Asn Thr Lys Ala Leu Ala Glu Gly Val Pro Ser Arg Phe Ser Gly
        50                  55                  60

Ser Gly Ser Gly Thr Gln Phe Ser Leu Lys Ile Asn Asn Leu Gln Pro
65                  70                  75                  80

Glu Asp Phe Gly Ile Tyr Tyr Cys Gln His His Tyr Asp Leu Pro Arg
                85                  90                  95

Thr Phe Gly Gly Gly Thr Lys Leu Glu Ile Lys Arg
            100                 105

<210> SEQ ID NO 5
<211> LENGTH: 117
<212> TYPE: PRT
```

<213> ORGANISM: mouse

<400> SEQUENCE: 5

```
Gln Val Gln Leu Lys Gln Ser Gly Pro Gly Leu Val Arg Pro Ser Gln
1               5                   10                  15

Ser Leu Ser Ile Thr Cys Thr Val Ser Gly Phe Pro Leu Gly Ile Phe
            20                  25                  30

Gly Val His Trp Val Arg Gln Ser Pro Gly Lys Gly Leu Glu Trp Leu
        35                  40                  45

Gly Val Ile Trp Lys Gly Gly Asn Thr Asp Tyr Asn Ala Ala Phe Met
    50                  55                  60

Ser Arg Leu Arg Ile Thr Lys Asp Asn Ser Lys Ser Gln Val Phe Phe
65                  70                  75                  80

Arg Met Asn Ser Leu Gln Thr Asp Asp Thr Ala Ile Tyr Tyr Cys Ala
                85                  90                  95

Lys Val Asn Leu Ala Asp Ala Met Asp Tyr Trp Gly Gln Gly Thr Ser
            100                 105                 110

Val Ile Val Ser Ser
        115
```

<210> SEQ ID NO 6
<211> LENGTH: 108
<212> TYPE: PRT
<213> ORGANISM: mouse

<400> SEQUENCE: 6

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Gly Tyr
            20                  25                  30

Leu Ala Trp Phe Gln Gln Lys Gln Gly Lys Ser Pro Gln Leu Leu Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Asp Leu Pro Arg
                85                  90                  95

Thr Phe Gly Gly Gly Thr Lys Leu Glu Ile Lys Arg
            100                 105
```

<210> SEQ ID NO 7
<211> LENGTH: 117
<212> TYPE: PRT
<213> ORGANISM: mouse

<400> SEQUENCE: 7

```
Gln Val Gln Leu Lys Gln Ser Gly Pro Gly Leu Val Arg Pro Ser Gln
1               5                   10                  15

Ser Leu Ser Ile Thr Cys Thr Val Ser Gly Phe Pro Leu Gly Thr Phe
            20                  25                  30

Gly Val His Trp Val Arg Gln Ser Pro Gly Lys Gly Leu Glu Trp Leu
        35                  40                  45

Gly Val Ile Trp Arg Gly Gly Asn Thr Asp Tyr Asn Ala Ala Phe Met
    50                  55                  60

Ser Arg Leu Arg Ile Thr Lys Asp Asn Ser Lys Ser Gln Val Phe Phe
65                  70                  75                  80
```

```
Arg Met Asn Ser Leu Gln Thr Asp Asp Thr Ala Ile Tyr Tyr Cys Ala
                85                  90                  95

Lys Val Asn Leu Ala Asp Ala Met Asp Tyr Trp Gly Gln Gly Thr Ser
            100                 105                 110

Val Ile Val Ser Ser
        115

<210> SEQ ID NO 8
<211> LENGTH: 108
<212> TYPE: PRT
<213> ORGANISM: mouse

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Gly Tyr
            20                  25                  30

Leu Ala Trp Phe Gln Lys Gln Gly Lys Ser Pro Gln Leu Leu Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His Tyr Asp Leu Pro Arg
                85                  90                  95

Thr Phe Gly Gly Gly Thr Lys Leu Glu Ile Lys Arg
            100                 105

<210> SEQ ID NO 9
<211> LENGTH: 5
<212> TYPE: PRT
<213> ORGANISM: mouse

<400> SEQUENCE: 9

Thr Tyr Ala Met Ser
1               5

<210> SEQ ID NO 10
<211> LENGTH: 5
<212> TYPE: PRT
<213> ORGANISM: mouse

<400> SEQUENCE: 10

Val Phe Gly Val His
1               5

<210> SEQ ID NO 11
<211> LENGTH: 5
<212> TYPE: PRT
<213> ORGANISM: mouse

<400> SEQUENCE: 11

Ile Phe Gly Val His
1               5

<210> SEQ ID NO 12
<211> LENGTH: 5
<212> TYPE: PRT
<213> ORGANISM: mouse

<400> SEQUENCE: 12

Thr Phe Gly Val His
```

```
<210> SEQ ID NO 13
<211> LENGTH: 16
<212> TYPE: PRT
<213> ORGANISM: mouse

<400> SEQUENCE: 13

Ser Ile Ser Thr Gly Asp Asn Thr Tyr Tyr Thr Asp Ser Val Arg Gly
1               5                   10                  15

<210> SEQ ID NO 14
<211> LENGTH: 16
<212> TYPE: PRT
<213> ORGANISM: mouse

<400> SEQUENCE: 14

Val Ile Trp Lys Gly Gly Asn Thr Asp Tyr Asn Ala Ala Phe Met Ser
1               5                   10                  15

<210> SEQ ID NO 15
<211> LENGTH: 16
<212> TYPE: PRT
<213> ORGANISM: mouse

<400> SEQUENCE: 15

Val Ile Trp Arg Gly Gly Asn Thr Asp Tyr Asn Ala Ala Phe Met Ser
1               5                   10                  15

<210> SEQ ID NO 16
<211> LENGTH: 11
<212> TYPE: PRT
<213> ORGANISM: mouse

<400> SEQUENCE: 16

Gly Arg Gly Asp Arg Gly Asp Leu Phe Gly Tyr
1               5                   10

<210> SEQ ID NO 17
<211> LENGTH: 9
<212> TYPE: PRT
<213> ORGANISM: mouse

<400> SEQUENCE: 17

Val Asn Leu Ala Asp Ala Met Asp Tyr
1               5

<210> SEQ ID NO 18
<211> LENGTH: 16
<212> TYPE: PRT
<213> ORGANISM: mouse

<400> SEQUENCE: 18

Lys Ser Ser Gln Ser Leu Leu Tyr Arg Gly Asn Gln Met Asn Tyr Leu
1               5                   10                  15

<210> SEQ ID NO 19
<211> LENGTH: 11
<212> TYPE: PRT
<213> ORGANISM: mouse

<400> SEQUENCE: 19

Arg Ser Ser Gly Asn Ile His Gly Tyr Leu Ala
1               5                   10
```

-continued

```
<210> SEQ ID NO 20
<211> LENGTH: 11
<212> TYPE: PRT
<213> ORGANISM: mouse

<400> SEQUENCE: 20

Arg Ala Ser Gly Asn Ile His Gly Tyr Leu Ala
1               5                   10

<210> SEQ ID NO 21
<211> LENGTH: 7
<212> TYPE: PRT
<213> ORGANISM: mouse

<400> SEQUENCE: 21

Trp Ala Ser Thr Arg Glu Ser
1               5

<210> SEQ ID NO 22
<211> LENGTH: 7
<212> TYPE: PRT
<213> ORGANISM: mouse

<400> SEQUENCE: 22

Asn Thr Lys Ala Leu Ala Glu
1               5

<210> SEQ ID NO 23
<211> LENGTH: 7
<212> TYPE: PRT
<213> ORGANISM: mouse

<400> SEQUENCE: 23

Asn Thr Lys Thr Leu Ala Glu
1               5

<210> SEQ ID NO 24
<211> LENGTH: 9
<212> TYPE: PRT
<213> ORGANISM: mouse

<400> SEQUENCE: 24

Gln Gln Tyr Tyr Thr Tyr Pro Arg Thr
1               5

<210> SEQ ID NO 25
<211> LENGTH: 9
<212> TYPE: PRT
<213> ORGANISM: mouse

<400> SEQUENCE: 25

Gln His His Tyr Asp Leu Pro Arg Thr
1               5

<210> SEQ ID NO 26
<211> LENGTH: 330
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
               35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 327
<212> TYPE: PRT
<213> ORGANISM: Homo sapiens

<400> SEQUENCE: 27

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
```

```
                         85                    90                    95
Arg Val Glu Ser Lys Tyr Gly Pro Pro Cys Pro Ser Cys Pro Ala Pro
                100                   105                   110

Glu Phe Leu Gly Gly Pro Ser Val Phe Leu Phe Pro Pro Lys Pro Lys
                115                   120                   125

Asp Thr Leu Met Ile Ser Arg Thr Pro Glu Val Thr Cys Val Val Val
            130                   135                   140

Asp Val Ser Gln Glu Asp Pro Glu Val Gln Phe Asn Trp Tyr Val Asp
145                   150                   155                   160

Gly Val Glu Val His Asn Ala Lys Thr Lys Pro Arg Glu Glu Gln Phe
                    165                   170                   175

Asn Ser Thr Tyr Arg Val Val Ser Val Leu Thr Val Leu His Gln Asp
                180                   185                   190

Trp Leu Asn Gly Lys Glu Tyr Lys Cys Lys Val Ser Asn Lys Gly Leu
                195                   200                   205

Pro Ser Ser Ile Glu Lys Thr Ile Ser Lys Ala Lys Gly Gln Pro Arg
            210                   215                   220

Glu Pro Gln Val Tyr Thr Leu Pro Pro Ser Gln Glu Glu Met Thr Lys
225                   230                   235                   240

Asn Gln Val Ser Leu Thr Cys Leu Val Lys Gly Phe Tyr Pro Ser Asp
                    245                   250                   255

Ile Ala Val Glu Trp Glu Ser Asn Gly Gln Pro Glu Asn Asn Tyr Lys
                260                   265                   270

Thr Thr Pro Pro Val Leu Asp Ser Asp Gly Ser Phe Phe Leu Tyr Ser
                275                   280                   285

Arg Leu Thr Val Asp Lys Ser Arg Trp Gln Glu Gly Asn Val Phe Ser
290                   295                   300

Cys Ser Val Met His Glu Ala Leu His Asn His Tyr Thr Gln Lys Ser
305                   310                   315                   320

Leu Ser Leu Ser Leu Gly Lys
                325

<210> SEQ ID NO 28
<211> LENGTH: 107
<212> TYPE: PRT
<213> ORGANISM: Homo sapiens

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 29
<211> LENGTH: 34
<212> TYPE: PRT
```

<210> SEQ ID NO 29
<211> LENGTH: (not shown)
<212> TYPE: PRT
<213> ORGANISM: Artificial
<220> FEATURE:
<223> OTHER INFORMATION: synthesized

<400> SEQUENCE: 29

Trp Met Glu Trp Asp Arg Glu Ile Asn Asn Tyr Thr Ser Leu Ile His
1               5                   10                  15
Ser Leu Ile Glu Glu Ser Gln Asn Gln Gln Glu Lys Asn Glu Gln Glu
            20                  25                  30
Leu Leu

<210> SEQ ID NO 30
<211> LENGTH: 36
<212> TYPE: PRT
<213> ORGANISM: Artificial
<220> FEATURE:
<223> OTHER INFORMATION: synthesized

<400> SEQUENCE: 30

Tyr Thr Ser Leu Ile His Ser Leu Ile Glu Glu Ser Gln Asn Gln Gln
1               5                   10                  15
Glu Lys Asn Glu Gln Glu Leu Leu Glu Leu Asp Lys Trp Ala Ser Leu
            20                  25                  30
Trp Asn Trp Phe
        35

<210> SEQ ID NO 31
<211> LENGTH: 39
<212> TYPE: PRT
<213> ORGANISM: Artificial
<220> FEATURE:
<223> OTHER INFORMATION: synthesized

<400> SEQUENCE: 31

Trp Gln Glu Trp Glu Gln Lys Ile Thr Ala Leu Leu Glu Gln Ala Gln
1               5                   10                  15
Ile Gln Gln Glu Lys Asn Glu Tyr Glu Leu Gln Lys Leu Asp Lys Trp
            20                  25                  30
Ala Ser Leu Trp Glu Trp Phe
        35

<210> SEQ ID NO 32
<211> LENGTH: 36
<212> TYPE: PRT
<213> ORGANISM: Artificial
<220> FEATURE:
<223> OTHER INFORMATION: Synthesized

<400> SEQUENCE: 32

Met Thr Trp Met Glu Trp Asp Arg Glu Ile Asn Asn Tyr Thr Ser Leu
1               5                   10                  15
Ile His Ser Leu Ile Glu Glu Ser Gln Asn Gln Gln Glu Lys Asn Glu
            20                  25                  30
Gln Glu Leu Leu
        35

<210> SEQ ID NO 33
<211> LENGTH: 38
<212> TYPE: PRT
<213> ORGANISM: Artificial
<220> FEATURE:
<223> OTHER INFORMATION: synthesized

<400> SEQUENCE: 33

-continued

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Glu Lys Asn Glu
                20                  25                  30

Ala Ala Leu Arg Glu Leu
            35

<210> SEQ ID NO 34
<211> LENGTH: 36
<212> TYPE: PRT
<213> ORGANISM: Artificial
<220> FEATURE:
<223> OTHER INFORMATION: synthesized

<400> SEQUENCE: 34

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg Ile Leu
            35

<210> SEQ ID NO 35
<211> LENGTH: 38
<212> TYPE: PRT
<213> ORGANISM: Artificial
<220> FEATURE:
<223> OTHER INFORMATION: synthesized

<400> SEQUENCE: 35

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
                20                  25                  30

Arg Tyr Leu Lys Asp Gln
            35

<210> SEQ ID NO 36
<211> LENGTH: 7
<212> TYPE: PRT
<213> ORGANISM: Artificial
<220> FEATURE:
<223> OTHER INFORMATION: linker

<400> SEQUENCE: 36

Leu Ser Leu Ser Pro Gly Lys
1               5

<210> SEQ ID NO 37
<211> LENGTH: 8
<212> TYPE: PRT
<213> ORGANISM: Artificial
<220> FEATURE:
<223> OTHER INFORMATION: linker

<400> SEQUENCE: 37

Leu Ser Pro Asn Arg Gly Glu Cys
1               5

<210> SEQ ID NO 38
<211> LENGTH: 15
<212> TYPE: PRT
<213> ORGANISM: Artificial
<220> FEATURE:

```
<223> OTHER INFORMATION: linker

<400> SEQUENCE: 38

Gly Gln Gln Gln Gly Gln Gln Gln Gly Gln Gln Gln Gln
1               5                   10                  15

<210> SEQ ID NO 39
<211> LENGTH: 16
<212> TYPE: PRT
<213> ORGANISM: Artificial
<220> FEATURE:
<223> OTHER INFORMATION: linker

<400> SEQUENCE: 39

Gly Gln Gln Gln Gly Gln Gln Gln Gly Gln Gln Gln Gln Gly
1               5                   10                  15

<210> SEQ ID NO 40
<211> LENGTH: 18
<212> TYPE: PRT
<213> ORGANISM: Artificial
<220> FEATURE:
<223> OTHER INFORMATION: linker

<400> SEQUENCE: 40

Gly Gln Gln Gln Gly Gln Gln Gln Gly Gln Gln Gln Gln Gly
1               5                   10                  15

Asn Asn

<210> SEQ ID NO 41
<211> LENGTH: 16
<212> TYPE: PRT
<213> ORGANISM: Artificial
<220> FEATURE:
<223> OTHER INFORMATION: linker

<400> SEQUENCE: 41

Gly Gly Gly Ser Gly Gly Gly Ser Gly Gly Gly Ser Gly Gly
1               5                   10                  15

<210> SEQ ID NO 42
<211> LENGTH: 16
<212> TYPE: PRT
<213> ORGANISM: Artificial
<220> FEATURE:
<223> OTHER INFORMATION: linker

<400> SEQUENCE: 42

Gly Gly Gly Ser Gly Gly Gly Ser Gly Gly Gly Ser Gly Asn
1               5                   10                  15

<210> SEQ ID NO 43
<211> LENGTH: 15
<212> TYPE: PRT
<213> ORGANISM: Artificial
<220> FEATURE:
<223> OTHER INFORMATION: linker

<400> SEQUENCE: 43

Ser Gly Gly Gly Gly Ser Gly Gly Gly Gly Ser Gly Gly Gly
1               5                   10                  15

<210> SEQ ID NO 44
<211> LENGTH: 16
<212> TYPE: PRT
<213> ORGANISM: Artificial
<220> FEATURE:
```

```
<223> OTHER INFORMATION: linker

<400> SEQUENCE: 44

Ser Gly Gly Gly Gly Ser Gly Gly Gly Gly Ser Gly Gly Gly Gly
1               5                   10                  15

<210> SEQ ID NO 45
<211> LENGTH: 17
<212> TYPE: PRT
<213> ORGANISM: Artificial
<220> FEATURE:
<223> OTHER INFORMATION: linker

<400> SEQUENCE: 45

Gly Ser Gly Gly Gly Gly Ser Gly Gly Gly Ser Gly Gly Gly Gly
1               5                   10                  15

Thr

<210> SEQ ID NO 46
<211> LENGTH: 17
<212> TYPE: PRT
<213> ORGANISM: Artificial
<220> FEATURE:
<223> OTHER INFORMATION: linker

<400> SEQUENCE: 46

Ser Gly Gly Gly Gly Ser Gly Gly Gly Gly Ser Gly Gly Gly Gly
1               5                   10                  15

Gly

<210> SEQ ID NO 47
<211> LENGTH: 18
<212> TYPE: PRT
<213> ORGANISM: Artificial
<220> FEATURE:
<223> OTHER INFORMATION: linker

<400> SEQUENCE: 47

Ser Gly Gly Gly Gly Ser Gly Gly Gly Gly Ser Gly Gly Gly Gly
1               5                   10                  15

Gly Thr

<210> SEQ ID NO 48
<211> LENGTH: 18
<212> TYPE: PRT
<213> ORGANISM: Artificial
<220> FEATURE:
<223> OTHER INFORMATION: linker

<400> SEQUENCE: 48

Ser Gly Gly Gly Gly Ser Gly Gly Gly Gly Ser Gly Gly Gly Gly
1               5                   10                  15

Gly Asn

<210> SEQ ID NO 49
<211> LENGTH: 18
<212> TYPE: PRT
<213> ORGANISM: Artificial
<220> FEATURE:
<223> OTHER INFORMATION: linker

<400> SEQUENCE: 49

Ser Gly Gly Gly Gly Ser Gly Gly Gly Gly Ser Gly Gly Gly Gly
1               5                   10                  15
```

Ala Ser

```
<210> SEQ ID NO 50
<211> LENGTH: 25
<212> TYPE: PRT
<213> ORGANISM: Artificial
<220> FEATURE:
<223> OTHER INFORMATION: linker

<400> SEQUENCE: 50

Ser Gly Gly Gly Gly Ser Gly Gly Gly Gly Ser Gly Gly Gly Gly Ser
1               5                   10                  15
Gly Gly Gly Gly Ser Gly Gly Gly Gly
            20                  25

<210> SEQ ID NO 51
<211> LENGTH: 26
<212> TYPE: PRT
<213> ORGANISM: Artificial
<220> FEATURE:
<223> OTHER INFORMATION: linker

<400> SEQUENCE: 51

Ser Gly Gly Gly Gly Ser Gly Gly Gly Gly Ser Gly Gly Gly Gly Ser
1               5                   10                  15
Gly Gly Gly Gly Ser Gly Gly Gly Gly Gly
            20                  25

<210> SEQ ID NO 52
<211> LENGTH: 27
<212> TYPE: PRT
<213> ORGANISM: Artificial
<220> FEATURE:
<223> OTHER INFORMATION: linker

<400> SEQUENCE: 52

Ser Gly Gly Gly Gly Ser Gly Gly Gly Gly Ser Gly Gly Gly Gly Ser
1               5                   10                  15
Gly Gly Gly Gly Ser Gly Gly Gly Gly Gly Gly
            20                  25

<210> SEQ ID NO 53
<211> LENGTH: 28
<212> TYPE: PRT
<213> ORGANISM: Artificial
<220> FEATURE:
<223> OTHER INFORMATION: linker

<400> SEQUENCE: 53

Ser Gly Gly Gly Gly Ser Gly Gly Gly Gly Ser Gly Gly Gly Gly Ser
1               5                   10                  15
Gly Gly Gly Gly Ser Gly Gly Gly Gly Gly Ala Ser
            20                  25

<210> SEQ ID NO 54
<211> LENGTH: 17
<212> TYPE: PRT
<213> ORGANISM: Artificial
<220> FEATURE:
<223> OTHER INFORMATION: linker

<400> SEQUENCE: 54

Gly Ser Ser Ser Ser Ser Ser Ser Ser Ser Ser Ser Ser Ser Ser Ser
1               5                   10                  15
Gly
```

<210> SEQ ID NO 55
<211> LENGTH: 19
<212> TYPE: PRT
<213> ORGANISM: Artificial
<220> FEATURE:
<223> OTHER INFORMATION: linker

<400> SEQUENCE: 55

Gly Ser Ser Ser Ser Ser Ser Ser Ser Ser Ser Ser Ser Ser Ser Ser
1               5                   10                  15

Gly Ala Ser

<210> SEQ ID NO 56
<211> LENGTH: 18
<212> TYPE: PRT
<213> ORGANISM: Artificial
<220> FEATURE:
<223> OTHER INFORMATION: linker

<400> SEQUENCE: 56

Gly Gly Gly Gly Ser Gly Gly Gly Gly Ser Gly Gly Gly Gly Ser Gly
1               5                   10                  15

Ala Ser

<210> SEQ ID NO 57
<211> LENGTH: 16
<212> TYPE: PRT
<213> ORGANISM: Artificial
<220> FEATURE:
<223> OTHER INFORMATION: linker

<400> SEQUENCE: 57

Gly Gly Gly Gly Ser Gly Gly Gly Gly Ser Gly Gly Gly Gly Ser Gly
1               5                   10                  15

<210> SEQ ID NO 58
<211> LENGTH: 26
<212> TYPE: PRT
<213> ORGANISM: Artificial
<220> FEATURE:
<223> OTHER INFORMATION: linker

<400> SEQUENCE: 58

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly
            20                  25

<210> SEQ ID NO 59
<211> LENGTH: 17
<212> TYPE: PRT
<213> ORGANISM: Artificial
<220> FEATURE:
<223> OTHER INFORMATION: linker

<400> SEQUENCE: 59

Gly Gly Gly Gly Ser Gly Gly Gly Gly Ser Gly Gly Gly Gly Ser Gly
1               5                   10                  15

Gly

<210> SEQ ID NO 60
<211> LENGTH: 27
<212> TYPE: PRT
<213> ORGANISM: Artificial

```
<220> FEATURE:
<223> OTHER INFORMATION: linker

<400> SEQUENCE: 60

Gly Gly Gly Gly Ser Gly Gly Gly Ser Gly Gly Gly Ser Gly
1               5                   10                  15

Gly Gly Gly Ser Gly Gly Gly Ser Gly Gly
            20                  25

<210> SEQ ID NO 61
<211> LENGTH: 6
<212> TYPE: PRT
<213> ORGANISM: Artificial
<220> FEATURE:
<223> OTHER INFORMATION: linker

<400> SEQUENCE: 61

Leu Ser Leu Ser Gly Gly
1               5

<210> SEQ ID NO 62
<211> LENGTH: 7
<212> TYPE: PRT
<213> ORGANISM: Artificial
<220> FEATURE:
<223> OTHER INFORMATION: linker

<400> SEQUENCE: 62

Leu Ser Leu Ser Pro Gly Gly
1               5

<210> SEQ ID NO 63
<211> LENGTH: 214
<212> TYPE: PRT
<213> ORGANISM: Homo sapiens

<400> SEQUENCE: 63

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Gly Tyr
            20                  25                  30

Leu Ala Trp Phe Gln Gln Lys Gln Gly Lys Ser Pro Gln Leu Leu Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Asp Leu Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

Ala Cys Glu Val Thr His Gln Gly Leu Ser Ser Pro Val Thr Lys Ser
            195                 200                 205

Phe Asn Arg Gly Glu Cys
        210

<210> SEQ ID NO 64
<211> LENGTH: 447
<212> TYPE: PRT
<213> ORGANISM: Homo sapiens

<400> SEQUENCE: 64

Gln Val Gln Leu Lys Gln Ser Gly Pro Gly Leu Val Arg Pro Ser Gln
1               5                   10                  15

Ser Leu Ser Ile Thr Cys Thr Val Ser Gly Phe Pro Leu Gly Ile Phe
            20                  25                  30

Gly Val His Trp Val Arg Gln Ser Pro Gly Lys Gly Leu Glu Trp Leu
        35                  40                  45

Gly Val Ile Trp Lys Gly Gly Asn Thr Asp Tyr Asn Ala Ala Phe Met
    50                  55                  60

Ser Arg Leu Arg Ile Thr Lys Asp Asn Ser Lys Ser Gln Val Phe Phe
65                  70                  75                  80

Arg Met Asn Ser Leu Gln Thr Asp Asp Thr Ala Ile Tyr Tyr Cys Ala
                85                  90                  95

Lys Val Asn Leu Ala Asp Ala Met Asp Tyr Trp Gly Gln Gly Thr Ser
            100                 105                 110

Val Ile Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 65
<211> LENGTH: 503
<212> TYPE: PRT
<213> ORGANISM: Homo sapiens

<400> SEQUENCE: 65

Gln Val Gln Leu Lys Gln Ser Gly Pro Gly Leu Val Arg Pro Ser Gln
1               5                   10                  15

Ser Leu Ser Ile Thr Cys Thr Val Ser Gly Phe Pro Leu Gly Ile Phe
            20                  25                  30

Gly Val His Trp Val Arg Gln Ser Pro Gly Lys Gly Leu Glu Trp Leu
        35                  40                  45

Gly Val Ile Trp Lys Gly Gly Asn Thr Asp Tyr Asn Ala Ala Phe Met
    50                  55                  60

Ser Arg Leu Arg Ile Thr Lys Asp Asn Ser Lys Ser Gln Val Phe Phe
65                  70                  75                  80

Arg Met Asn Ser Leu Gln Thr Asp Asp Thr Ala Ile Tyr Tyr Cys Ala
                85                  90                  95

Lys Val Asn Leu Ala Asp Ala Met Asp Tyr Trp Gly Gln Gly Thr Ser
            100                 105                 110

Val Ile Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

-continued

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gln Gln Gln Gln Gly Gln Gln Gln Gly Gln Gln Gln Gly Asn
450                 455                 460

Asn Thr Thr Trp Glu Ala Trp Asp Arg Ala Ile Ala Glu Tyr Ala Ala
465                 470                 475                 480

Arg Ile Glu Ala Leu Ile Arg Ala Ala Gln Glu Gln Gln Glu Lys Asn
                485                 490                 495

Glu Ala Ala Leu Arg Glu Leu
            500

<210> SEQ ID NO 66
<211> LENGTH: 345
<212> TYPE: PRT
<213> ORGANISM: Human immunodeficiency virus

<400> SEQUENCE: 66

Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn His Thr Thr Trp Met Glu Trp Asp Arg Glu Ile Asn Asn Tyr Thr
        115                 120                 125

Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160
```

```
Trp Phe Asn Ile Thr Asn Trp Leu Trp Tyr Ile Lys Leu Phe Ile Met
                165                 170                 175
Ile Val Gly Gly Leu Val Gly Leu Arg Ile Val Phe Ala Val Leu Ser
                180                 185                 190
Ile Val Asn Arg Val Arg Gln Gly Tyr Ser Pro Leu Ser Phe Gln Thr
            195                 200                 205
His Leu Pro Thr Pro Arg Gly Pro Asp Arg Pro Glu Gly Ile Glu Glu
        210                 215                 220
Glu Gly Gly Glu Arg Asp Arg Asp Arg Ser Ile Arg Leu Val Asn Gly
225                 230                 235                 240
Ser Leu Ala Leu Ile Trp Asp Asp Leu Arg Ser Leu Cys Leu Phe Ser
                245                 250                 255
Tyr His Arg Leu Arg Asp Leu Leu Leu Ile Val Thr Arg Ile Val Glu
                260                 265                 270
Leu Leu Gly Arg Arg Gly Trp Glu Ala Leu Lys Tyr Trp Trp Asn Leu
            275                 280                 285
Leu Gln Tyr Trp Ser Gln Glu Leu Lys Asn Ser Ala Val Ser Leu Leu
        290                 295                 300
Asn Ala Thr Ala Ile Ala Val Ala Glu Gly Thr Asp Arg Val Ile Glu
305                 310                 315                 320
Val Val Gln Gly Ala Cys Arg Ala Ile Arg His Ile Pro Arg Arg Ile
                325                 330                 335
Arg Gln Gly Leu Glu Arg Ile Leu Leu
            340                 345
```